(12) United States Patent
Lanctot et al.

(10) Patent No.: US 6,830,885 B1
(45) Date of Patent: Dec. 14, 2004

(54) NUCLEIC ACID MOLECULE, METHOD AND KIT FOR SELECTING A NUCLEIC ACID HAVING A DESIRED FEATURE

(75) Inventors: Christian Lanctot, Montreal (CA); Pierre Moffat, Lachine (CA); Patrick Salois, Montreal (CA)

(73) Assignee: Phenogene Therapeutiques Inc., Montreal (CA)

( * ) Notice: Subject to any disclaimer, the term of this patent is extended or adjusted under 35 U.S.C. 154(b) by 198 days.

(21) Appl. No.: 09/641,931

(22) Filed: Aug. 18, 2000

(51) Int. Cl.[7] .................................................. C12Q 1/68
(52) U.S. Cl. .................... 435/6; 435/69.1; 435/69.7; 435/243; 435/320.1; 435/456; 435/475; 435/477
(58) Field of Search ........................ 435/6, 69.1, 69.7, 435/243, 320.1, 325, 456, 475, 477, 91.1, 172.3; 424/218.1; 536/23.1, 23.4

(56) References Cited

U.S. PATENT DOCUMENTS

| | | | | |
|---|---|---|---|---|
| 5,217,879 A | * | 6/1993 | Huang et al. | ............... 435/69.1 |
| 6,150,098 A | * | 11/2000 | Zhang et al. | ................... 435/6 |

FOREIGN PATENT DOCUMENTS

| | | |
|---|---|---|
| WO | WO 97/32017 | 9/1997 |
| WO | WO 9925876 | 5/1999 |
| WO | WO 99/25876 | 5/1999 |
| WO | WO 9936516 | 7/1999 |

OTHER PUBLICATIONS

Flint et al. Principles of Virology: Molecular Biology, Pathogenesis, and Control. Washington D.C.: ASM Press. 2000, p. 452.*

Seed, B "Developments in expression cloning" Current Opinion in Biotechnology 1995, 6: 567–573.*

Parks, R. J.; Chen, L.; Anton, M.; Sankar, U.; Rudnicki, M. A.; Graham, F. L. "A helper–dependent adenovirus vector system: Removal of helper virus by Cre–mediated excision of the viral packaging signal" PNAS 1996, 93, 13565–13570.*

Jung, S., et al., "Selectively infective phage (SIP) technology: scope and limitations"; Journal of Immunological Methods, Elsevier Science Publishers, Publishers B.V., Amsterdam, NL, vol. 231, No. 1–2, Dec. 10, 1999, pp. 93–104.

Tashiro, K., Tada, H., Heilker, R., Shirozu, M., Nakano, T., Honjo, T. (1993) Signal sequence trap : a cloning strategy For secreted proteins and type I membrane proteins, Science, 261, 600–602.

Filocamo G., Pacini, L., Migliaccio, G. (1997) Chimeric Sindbis viruses dependent on the NS3 protease of hepatitis C virus, J. Virol., 71, 1417–1427.

Cho, Y.–G., Moon, H.–S., Sun, Y.C. (1997) Construction of hepatitis C–SIN virus recombinants with replicative dependency on hepatitis C virus serine protease activity, J. Virol. Meth., 65,201–207.

Strauss, E.G., Rice, C.M., Strauss, J.H. (1984) Complete nucleotide sequence of the genomic RNA of Sindbis virus, Virology, vol. 133, 92–110.

* cited by examiner

Primary Examiner—Bennett Celsa
Assistant Examiner—Jon D. Epperson
(74) Attorney, Agent, or Firm—Charles E. Lyon; D. Phil; Brenda Herschbach Jarrell

(57) ABSTRACT

This invention relates to the screening of nucleic acids. More particularly, the present invention provides a dysfunctional viral genome capable of both expressing libraries of exogenous nucleic acids and selecting the sequences having a predefined characteristic or function within the cell, such as nucleic acids encoding signal peptides, secreted proteins, membrane bound proteins, proteases and drug-resistance proteins. The invention further provides a method and a kit for selecting nucleic acids having a desired feature, wherein production of a viral particle is dependent on insertion of an exogenous nucleic acid having the desired feature into a dysfunctional viral genome or into a viral genome exposed to a substance inhibiting viral packaging function(s).

12 Claims, 20 Drawing Sheets

FIGURE 5A

...tcgatccgaattc GCGGCCGC tctatt GGATCC tcgagcaga TCT GCA GCA...

NotI      BamHI       $S_1$   $A_2$   $A_3$

AGA TGA atcaagcttatcgataccgtcgagcatgcatctaggtg
tccaagccatcagagaggggaaataaagcatctctacggtggtcctaaatagtcagcatagt acatttcatctgactaatactacaacaccaccaccacc ATG AAT AGA SG2 (-46/+14)                            $Met_i$ $N_2$ $R_3$

...GAG TGG TCC GCA TGG TGA......

SwaI

...$(A)_{32}$ggggaatttcgcgATTTAAATt...

S   A   A   P   L   V   T   A   M   C   L   L   G   N   V   S
       tct gca gca cca ctg gtc acg gca atg tgt ttg ctc gga aat gtg agc p62mutRS S   A   A   P   L   V   T   A   M   C   R   S   G   N   V   S
       tct gca gca cca ctg gtc acg gca atg tgt cgg agc gga aat gtg agc

NUCLEIC ACID MOLECULE, METHOD AND KIT FOR SELECTING A NUCLEIC ACID HAVING A DESIRED FEATURE

BACKGROUND OF THE INVENTION a) Field of the Invention

The present invention relates to screening of nucleic acids. More particularly, the present invention is concerned with the identification of nucleic acids having a desired feature, such as nucleic acids encoding signal peptides, secreted proteins, membrane bound proteins, proteases and drug-resistance proteins.

b) Brief Description of the Prior Art

Large-scale gene sequencing projects are currently generating huge amounts of genetic information. Biomedical research is therefore faced with the challenge of deciphering this genetic information. This is usually done with the help of functional genomic tools. There are currently two main approaches to massively analyze gene function. The first one involves determining the expression profile of genes in normal and diseased tissues. This approach only gives circumstantial evidence to gene function and allows at best the formulation of hypotheses with respect to the function of differentially expressed genes. The other approach is a more biological approach and it uses model organism or cell-based assays to selectively identify genes possessing a chosen biological property or function. Both approaches are complementary and ultimately converge toward the characterization of therapeutically useful genes.

Cell-based screening technology can be viewed as a tool that sends out a positive "signal" if, and only if, a particular "target" gene possessing the activity being screened for has been incorporated into a cell. This technology is based on a reporter system that is kept inactive in the absence of the target gene. Although the nature of the reporter and the conditions upon which it is activated may vary, the reporter systems typically involve the synthesis of either marker proteins (e.g. antibodies), proteins necessary for cell survival under selective conditions (e.g. aminoglycoside3' phosphotransferase), or fluorescent tags such as green fluorescent protein. In every case, a cell selection procedure is required to identify the gene which has activated the reporter. When screening is conducted with micro-organisms (e.g. *Escherchia coli, Saccharomyces cerevisiae*), the cell selection step is relatively straightforward. However, mammalian cells are the model of choice to study genes involved in human diseases and, unlike micro-organisms, mammalian cells cannot be easily selected in culture. Methods for selecting mammalian cells either require sophisticated and expensive hardware (e.g. fluorescence-activated cell sorting) or are lengthy and susceptible to high percentages of false-positives due to mutation/adaptation (growth of cells in selective medium). Furthermore, these known methods cannot greatly amplify the exogenous nucleic acid encoding a protein of interest since it gives rise to at most a few cells in which the reporter has been activated.

Viruses have been used for many years to introduce and express exogenous coding sequences in a host cell. Among the viruses used, recombinant Sindbis virus described in U.S. Pat. No 5,217,879 is particularly useful since it can infect cells from various different tissues and express an exogenous coding sequence at relatively high levels. Recently, the scientific community has foreseen the potential of viruses in gene screening methods, particularly as a mean to introduce genes into mammalian cells. International patent application No. PCT/US99/01164 published under No. WO99/36516 describes the use of virus vectors for selecting desired functions of RNAs and proteins. Similarly, International patent application No. PCT/US98/24520 published under No. WO99/25876 describes a method for the detection, characterization and isolation of nucleic acids encoding proteins of a desired property. These methods are based on the expression of high levels of an exogenous protein in a cell and on the marking or observance of the exogenous protein so produced to determine its function. Therefore, the methods described in these two international applications are different from the present invention. Indeed, these international applications do not describe a method wherein viral particles are produced only once an exogenous nucleic acid having a desired property has been inserted into a viral genome. They do not describe either a nucleic acid molecule encoding a dysfunctional viral genome wherein production of a viral particle is dependent on insertion into the dysfunctional viral genome of an exogenous nucleic acid having a desired property such as a nucleic acid encoding a signal peptide, a secreted protein, a membrane protein, a protease or a drug-resistance protein.

In view of the above, it is clear that there is a need for methods and tools which overcome the limits and obviate the problems known in the art. More particularly, there is a need for a gene screening method that bypasses the time-consuming cell selection step and that does not require marking of proteins. The purpose of this invention is to fulfill these needs by taking advantage of the natural property of viruses to incorporate and export genetic material out of a cell. The purpose of this invention is also to fulfil other needs that will be apparent to those skilled in the art upon reading the following specification.

SUMMARY OF THE INVENTION

It is therefore an object of the present invention to provide a molecule, a method and a kit for selecting a nucleic acid having a desired feature. More particularly, it is an object of the invention to provide a modified viral genome capable of both expressing exogenous nucleic acids within a host and selecting among these nucleic acids the ones having a desired feature, a predefined characteristic or function. Such nucleic acids include nucleic acids encoding a signal peptide, nucleic acids encoding at least partially for a protein having a signal peptide, nucleic acids encoding proteases, nucleic acids encoding proteins or peptides having a proteolytic activity and nucleic acids encoding drug-resistance proteins or peptides.

In one aspect, the invention is directed to a method for selecting a nucleic acid having a desired feature and the method comprises the steps of:

a) providing a viral genome capable, when present into a suitable host, of expressing an exogenous nucleic acid inserted therein and also capable of packaging itself into a viral particle;

b) providing a suppressive condition wherein the viral genome is capable of packaging itself into a viral particle only once said suppressive condition is being overcome;

c) inserting an exogenous nucleic acid into the viral genome to provide a recombinant viral genome;

d) transfecting the recombinant viral genome into a suitable host; and e) allowing the recombinant viral genome to express said exogenous nucleic acid and package itself into a recombinant viral particle. The production of at least one recombinant viral particle is then indicative that the suppressive condition has been overcome and that the exogenous nucleic acid inserted in step c) has the desired feature.

Preferably, the suppressive condition is provided by modifying the viral genome in order to inactivate a viral gene product involved in the packaging of the viral particle (s). The viral genome can also be modified to abolish its autoreplicative functions(s) and/or the infectivity of viral particles produced therefrom.

In one embodiment, the viral genome is modified in order to encode a dysfunctional signal peptide and the production of a viral particle is dependent on insertion into said viral genome of an exogenous nucleic acid encoding a functional signal peptide or at least partially a protein having a signal peptide. It is therefore possible to select a nucleic acid encoding a signal peptide or a protein having a signal peptide using the method of the invention. The present invention thus also provides a method for selecting a nucleic acid encoding a signal peptide or a protein having a signal peptide, this method comprising the steps of:

a) providing a viral genome modified in order to encode a dysfunctional signal peptide and wherein production of a viral particle is dependent on the expression of a functional signal peptide;

b) inserting an exogenous nucleic acid into the nucleic acid encoding the dysfunctional signal peptide to provide a recombinant viral genome;

c) transfecting the recombinant viral genome of step b) into a suitable host; and d) allowing the recombinant viral genome to express the exogenous nucleic acid and package itself into a recombinant viral particle, whereby production of at least one recombinant viral particle is indicative that the exogenous nucleic acid inserted in step b) encodes a signal peptide or a protein having a signal peptide.

In an other embodiment, the viral genome is modified in order to encode a fusion protein comprising a structural viral protein bound to a fetter-protein and the production of a viral particle is dependent on liberation of said structural viral protein from said fetter-protein. It is therefore possible to select a nucleic acid encoding a protease, or encoding a protein or a peptide having a proteolytic activity using the method of the invention. The present invention thus further provides a method for selecting a nucleic acid encoding a signal peptide or a protein having a signal peptide, this method comprising the steps of:

a) providing a viral genome modified in order to encode a fusion protein comprising a structural viral protein bound to a fetter-protein, wherein production of a viral particle is dependent on liberation of the structural viral protein from the fetter-protein;

b) inserting an exogenous nucleic acid into the viral genome of step a) in order to provide a recombinant viral genome;

c) transfecting the recombinant viral genome of step b) into a suitable host; and d) allowing the recombinant viral genome to express the exogenous nucleic acid and package itself into a recombinant viral particle. The production of at least one recombinant viral particle is then indicative that the exogenous nucleic acid inserted in step b) encodes a peptide or a protein having a proteolytic activity or a protease capable of liberating said structural viral protein from said fetter-protein.

The suppressive condition can also be provided by exposing the transfected host to a substance inhibiting viral packaging function(s) such as cerulenin and okadaic acid. The present invention thus further provides a method for selecting a nucleic acid encoding a drug-resistance protein or peptide, this method comprising the steps of:

a) providing a viral genome encoding a viral particle, said viral genome when present into a suitable host having the abilities of:

i) expressing an exogenous nucleic acid inserted therein; and ii) packaging said exogenous nucleic acid into a recombinant viral particle;

b) inserting an exogenous nucleic acid into the viral genome to provide a recombinant viral genome;

c) transfecting said recombinant viral genome into a suitable host; and d) exposing the host transfected in step c) to a substance inhibiting viral packaging function(s), e) allowing the recombinant viral genome to express the exogenous nucleic acid and package itself into a recombinant viral particle. The production of at least one recombinant viral particle is then indicative that the exogenous nucleic acid inserted in step b) encodes a drug-resistance protein or peptide.

Although, theoretically, any viral genome could be used according to the present invention, viruses of the group of RNA viruses are preferred, and more preferably members of the Alphavirus family such as the Sindbis virus or the Semliki forest virus. Preferably the viral genome used is also capable of autoreplication and insertion therein of an exogenous nucleic acid having a desired feature results in the production of a clonal population of recombinant viral particles. It is also preferable to incorporate the viral genome into a vector such as a bacterial plasmid in order to facilitate the insertion of exogenous nucleic acids and the modification of the viral genome.

In another aspect, the invention is directed to an isolated nucleic acid molecule encoding a dysfunctional viral genome. Using the isolated nucleic acid molecule of the invention, the production of a viral particle is dependent on: 1) insertion of an exogenous nucleic acid having a desired feature into the nucleic acid molecule of the invention; and 2) introduction of this nucleic acid molecule incorporating the exogenous nucleic acid into a suitable host.

In a further aspect, the invention is directed to a kit for selecting a nucleic acid having a desired feature, this kit comprising:

a nucleic acid molecule encoding a dysfunctional viral genome according to the present invention; and at least one further element selected from the group consisting of instructions for using said kit, reaction buffer(s), enzyme(s), probe(s) and pool(s) of exogenous nucleotide sequences.

Also encompassed within the invention is a N-terminal amino acid sequence encoding a dysfunctional signal peptide of a viral envelope protein. This dysfunctional signal peptide has the characteristics of allowing viral envelope proteins association without directing said viral envelope protein into the cellular secretory pathway and across the lipid bilayer of a host cell.

An advantage of the present invention is that it takes advantage of the natural property of viruses to export genetic material out of a cell. Accordingly, it obviates the expensive and time-consuming task of selecting cells that express a gene of interest. The invention is also much more rapid, efficient and accurate for selecting a particular nucleic acid having a desired feature, characteristic or function. The invention can also selectively retrieve from a library of nucleic acids a nucleic acid having a desired feature among a pool of nucleic acids.

Other objects and advantages of the present invention will be apparent upon reading the following non-restrictive description of several preferred embodiments, made with reference to the accompanying drawings.

BRIEF DESCRIPTION OF THE DRAWINGS

FIGS. 5A, 5B, 5C, 5D, and 5E show sequences of some regions of the modified viral genome of FIG. 3A.

Figure 1:
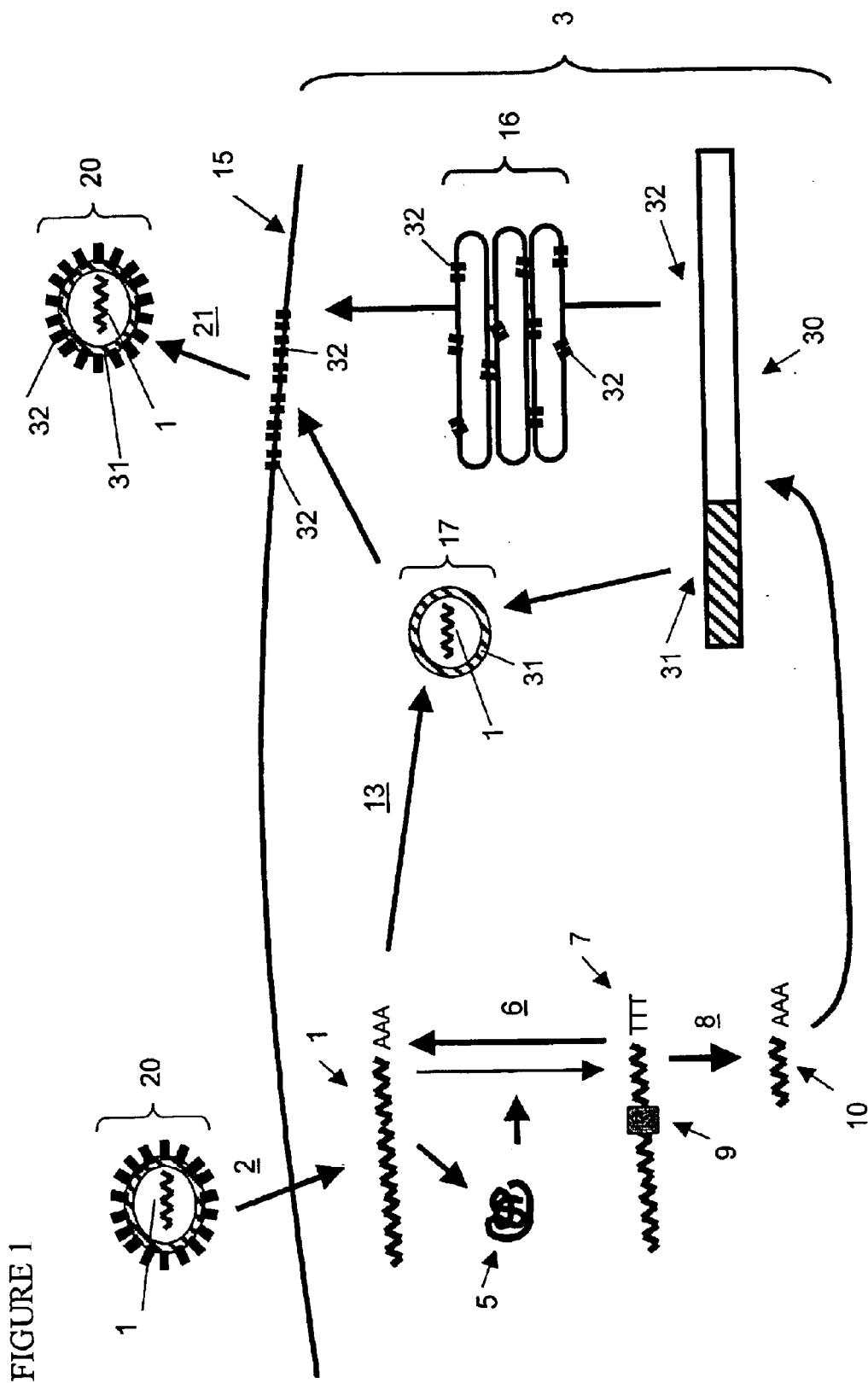
FIG. 1 schematizes the Sindbis virus life cycle.

Similar references are used in different figures to denote similar components.

DETAILED DESCRIPTION OF THE INVENTION

A) Definitions

Throughout the text, the word "kilobase" is generally abbreviated as "kb", the words "deoxyribonucleic acid" as "DNA", the words "ribonucleic acid" as "RNA", the words "complementary DNA" as "cDNA", the words "polymerase chain reaction" as "PCR", and the words "reverse transcription" as "RT". Nucleotide sequences are written in the 5' to 3' orientation unless stated otherwise.

In order to provide an even clearer and more consistent understanding of the specification and the claims, including the scope given herein to such terms, the following definitions are provided:

Complete/Functional: The terms "complete" or "functional" in association with "viral genome", "recombinant viral genome", refer to the ability of a viral genome (recombinant or not) to produce viral particles incorporating said genome when introduced into a suitable host. Although preferable, autoreplication and/or infectiousness is not one of the compulsory characteristics of a functional viral particle.

Desired feature: Refers to a nucleic acid encoding a peptide or a protein having a desired property. Examples of a nucleic acid having a "desired property" includes a nucleic acid encoding a specific amino acid sequence (e.g. a signal peptide sequence found in a secreted or membrane-bound protein), a specific enzymatic activity (e.g. a protease), a specific cellular function (e.g. a drug-resistance protein), etc.

Drug-resistanc: Refers to the ability of a protein, a protein fragment or a peptide to suppress or inhibit negative effects caused by a drug or a similar substance. A drug-resistance protein, protein fragment, or peptide may act directly on the drug itself or indirectly by acting on the target(s) of the drug.

Dysfunctional viral genome: These terms refer to a nucleic acid encoding components of a viral particle and being capable of expressing an exogenous nucleic acid inserted therein when it is inserted into a suitable host, but being incapable of packaging itself into complete or functional viral particles. In some instances, the "dysfunctional viral genome" may also be incapable of autoreplication. A "dysfunctional viral genome" can be obtained by genetically manipulating a DNA or RNA molecule derived from a eukaryotic virus such that assembly, packaging and/or release of viral particles is rendered defective.

Exogenous nucleic acid: A nucleic acid (such as cDNA, cDNA fragments, genomic DNA fragments, antisense RNA, oligonucleotide) which is not naturally part of another nucleic acid molecule. The "exogenous nucleic acid" may be from any organism or purely synthetic. Typically, the "exogenous nucleic acid" encodes a non-viral sequence. However, the term "exogenous" can also include virus sequences if the invention is used to screen viral nucleic acids.

Expression: The process whereby an exogenous nucleic acid is transcribed. In the case of cDNAs, cDNA fragments and genomic DNA fragments, the transcribed exogenous nucleic acid is subsequently translated into a peptide or a protein in order to carry out its function if any.

Fetter-protein: A protein that is fused to a viral protein having important viral function(s). According to an embodiment of the present invention, a fetter-protein is bound to a viral structural protein in order to block the normal packaging function(s) of the viral structural protein.

Fusion protein: A protein formed by the expression of a hybrid gene made by combining two gene sequences. Typically, this is accomplished by cloning a cDNA into an expression vector in frame with an existing gene.

Host: A cell, tissue, organ or organism capable of providing cellular components for allowing the expression of an exogenous nucleic acid embedded into a vector or a viral genome, and for allowing the production of viral particles encoded by such vector or viral genome. This term is intended to also include hosts which have been modified in order to accomplish these functions. Bacteria, fungi, animal (cells, tissues, or organisms) and plant (cells, tissues, or organisms) are examples of a host.

Infectiousness: The ability of a viral particle to penetrate into and infect a host by introducing into the host its viral genome.

Insertion: The process by which a nucleic acid is introduced into another nucleic acid. A typical example includes insertion of an exogenous nucleic acid into a viral genome to create a "recombinant" viral genome. Methods for inserting a nucleic acid into another normally requires the use of restriction enzymes and such methods of insertion are well known in the art.

Library: A collection or a pool of nucleic acid molecules. This includes genomic libraries, RNA libraries, cDNA libraries, expressed sequence tag libraries, artificial sequences libraries including randomized artificial sequence libraries.

Membrane bound protein: A protein that is anchored to the membrane of a cell, with regions permanently attached to a membrane or inserted into a membrane. Important examples include hormone receptors, ion channels and transport proteins. Membrane bound proteins are normally co-translationally directed to the cell membrane by the presence of a signal peptide.

Modified viral genome: A recombinant DNA or RNA molecule derived from an eukaryotic virus and which has been genetically manipulated. According to preferred embodiments of the present invention, the modified viral genome has been modified such that assembly, packaging and/or release of viral particles have been rendered defective without affecting self-replication functions.

Nucleic acid: Any DNA, RNA sequence or molecule having one nucleotide or more, including nucleotide sequences encoding a complete gene. The term is intended to encompass all nucleic acids whether occurring naturally or non-naturally in a particular cell, tissue or organism. This includes DNA and fragments thereof, RNA and fragments thereof, cDNAs and fragments thereof, expressed sequence tags, artificial sequences including randomized artificial sequences.

Packaging: The process by which the genetic material of a virus (the viral genome) is encapsulated into virus capsid proteins. As used herein, the term packaging also includes the steps which are normally necessary such that encapsulated viral genomes are released from a host into the extracellular medium.

Protease: Any enzyme that catalyses the splitting of interior peptide bonds in a protein.

Proteolytic activity: Any activity pertaining to proteolysis, characterized by proteolysis, triggering proteolysis or promoting proteolysis i.e. the splitting of proteins by hydrolysis of the peptide bonds with formation of smaller polypeptides.

Recombinant The term "recombinant" in association with "viral genome" or "viral particle" refers to a viral genome which has been modified to contain a non-native exogenous nucleic acid.

Replication: The process which involves the production of full-length equivalents of plus polarity of a viral genome using a minus strand as a template.

Secreted protein: any protein initially synthesized bearing a signal peptide. Typically, the signal peptide is removed shortly after its synthesis.

Signal peptide: a peptide capable of directing a nascent protein to the cell secretory pathway. It is generally accepted that a signal peptide is composed of an initiating methionine, a highly hydrophobic stretch, typically 10 to 15 residues long, and a signal peptidase cleavage site.

Structural viral protein: any protein involved in the packaging, assembly and/or release of a viral particle.

Suppressive condition: A condition by which a normal function is inhibited or blocked. Examples include the treatment of cells or organisms with a drug to inhibit specific cellular activities, and the introduction of mutation(s) into a viral genome for inactivating one or many genes and thereby block or attenuate the normal packaging functions of the virus. According to the present invention, a suppressive condition is said to be overcome when a viral genome is capable of packaging itself into at least one viral particle.

Transfection: the process of introducing nucleic acids in eukaryotic cells by any means such as electroporation, lipofection, precipitate uptake, micro-injection. A cell having incorporated an exogenous nucleic acid is said to be transfected.

Vector: A self-replicating RNA or DNA molecule which can be used to transfer an RNA or DNA segment from one organism to another. Vectors are particularly useful for manipulating genetic constructs and different vectors may have properties particularly appropriate to express protein(s) in a recipient during cloning procedures and may comprise different selectable markers. Bacterial plasmids are commonly used vectors.

Viral genome: Refers to total set of genes which are necessary to produce a viral particle. Most viral genomes which are used have been modified using molecular biology techniques in order to include cloning sites.

Viral particle: an agent, preferably but not essentially infectious, composed of a nucleic acid (e.g. viral genome or a recombinant viral genome) encapsulated into a protein coat.

B) General Overview of the Invention

The invention is based on the use of a viral genome to selectively package an exogenous nucleic acid having a desired feature into a viral particle. More particularly, the invention uses a "selection" process wherein 1) an exogenous nucleic acid is inserted into a viral genome and 2) a suppressive condition is established such that production of viral particles is impaired. If the exogenous nucleic acid inserted has a predefined characteristic or function, its expression triggers production of at least one, preferably a plurality of viral particles. If the exogenous nucleic acid inserted does not have the predefined characteristic or function, it does not lead to formation of a viral particle.

In one aspect, the present invention relates to a method for selecting a nucleic acid having a desired feature. Such a method is particularly useful for identifying eukaryotic cDNAs or cDNA fragments and proteins or peptides encoded thereby. The method of the invention is also both more effective and more rapid than any gene screening method known in the art. Examples of genes which can be rapidly identified with the method of the present invention include genes encoding secreted proteins, membrane bound proteins, proteases, proteins or peptides having a proteolytic activity and drug-resistance proteins.

In a second aspect, the present invention relates to a nucleic acid molecule encoding a dysfunctional viral genome wherein production of a viral particle is dependent on insertion of an exogenous nucleic acid having a desired feature into the dysfunctional viral genome.

In a third aspect, the present invention relates to a kit for selecting a nucleic acid having a desired feature, the kit comprising a nucleic acid molecule encoding a dysfunctional viral genome according to the invention and at least one element selected from the group consisting of instructions for using the kit, reaction buffer(s), enzyme(s), probe (s) and pool(s) of exogenous nucleotide sequences.

In a forth aspect, the present invention relates to a N-terminal amino acid sequence encoding a dysfunctional signal peptide of a viral envelope protein. This signal peptide is characterized in that it allows normal association of viral envelope proteins without directing these viral envelope protein into the regular cellular secretory pathway and across the lipid bilayer of a host cell.

C) Methods for Selecting a Nucleic Acid Having a Desired Feature

The present invention describes methods to screen and select exogenous nucleic acids having a desired feature such as nucleic acids encoding a protein having a predefined function or characteristic. One important component of the methods provided by the present invention is the use of recombinant viral genomes to select and export from a host a nucleic acid of interest. This is achieved by using a viral genome which selectively packages in viral particles an exogenous nucleic acid expressed from the viral genome and having a desired feature. According to the invention, production of a viral particle is indicative that a suppressive condition has been overcome and that the exogenous nucleic acid inserted has the desired feature.

In its most basic version, the method of the invention comprises the steps of:
  a) providing a viral genome capable, when present into a suitable host, of expressing an exogenous nucleic acid inserted therein and also capable of packaging itself or a copy of itself into at least one, preferably a plurality, of viral particles;
  b) providing a suppressive condition wherein the viral genome is capable of packaging itself (or a copy of itself) into a viral particle only once the suppressive condition is being overcome;
  c) inserting into the viral genome an exogenous nucleic acid to provide a recombinant viral genome;
  d) inserting the recombinant viral genome of step c) into a suitable host and;
  e) allowing the recombinant viral genome to express the exogenous nucleic acid and package the recombinant viral genome into at least one, preferably a plurality, of viral particles. Production of recombinant viral particle (s) is indicative that the suppressive condition has been overcome and that the exogenous nucleic acid inserted in step c) has the desired feature.

i) The Viral Genome

As it will now be explained in more detail, the present invention uses a viral genome and viral particles as tools for screening and selecting nucleic acids encoding a predefined function or having a desired feature.

Theoretically, any viral genome can be used according to the present invention. However, the viral genome, once inserted into a suitable host, must fulfill the following requirements:
  a) be able to express an exogenous nucleic acid inserted therein;
  b) preferably, be able to autoreplicate;
  c) be able to package the exogenous nucleic acid into at least one, preferably a plurality, of recombinant viral particles without being able to produce viral particle(s) on its own under a predefined suppressive condition.

Viruses of the group of RNA viruses are preferred according to the present invention. More preferably, this invention uses members of the Alphavirus family such as Sindbis virus, Semliki forest virus and Venezuelan equine encephalitis virus. Most preferably, the genome of Sindbis virus is used. The Sindbis genome is preferred and used in the following examples because it is well-characterized and relatively small and simple. Furthermore, it can be easily manipulated in vitro using standard recombinant DNA technology and it has a broad host cell range (e.g. neurons, epithelial cells, and fibroblasts of mammalian origin, including human), thereby allowing expression screening in the cell line most appropriate for the characteristic or function being screened for. In the present invention, preferred hosts are BHK-21 fibroblast cells, a cell line that efficiently supports Sindbis life cycle. However, the invention is not limited to the Sindbis virus. Indeed, it is expected that a person skilled in the art could, upon some experimentation, achieve similar results than those obtained with the Sindbis virus, using other types of viruses such as other alphaviruses (e.g. Semliki Forest virus), other single stranded RNA viruses (e.g. Rous sarcoma virus, influenza virus, Brome mosaic virus, poliovirus), and other viruses (e.g. adenovirus, potyvirus, tobamovirus, bromovirus, geminivirus, rhinovirus, simianvirus)

The Sindbis virus is well known and its life cycle is summarized in FIG. 1. Briefly, Sindbis viral particles (20) comprise a viral genome (1) of 11,703 nucleotides (Strauss et al., 1984). This viral genome serves directly as a messenger RNA upon infection (2) of a host cell (3). Upon infection of the cell, the viral genome (1) is uncoated and translation of sequences encoding non-structural viral proteins (5) occurs. The first non-structural proteins to be produced are nsP1-nsP4 which replicate the viral messenger RNA (1) through the synthesis (6) of a full length minus strand (7) complementary to the genomic RNA (1). This complementary RNA (7) also serves as template for the synthesis (8) of a 4,103 nucleotides subgenomic messenger RNA (10) corresponding to the 3' end of the viral genome, from a so-called "subgenomic" promoter (9). The subgenomic mRNA (10) is polycistronic and encodes a structural polyprotein precursor (30) comprising a viral capsid protein (31) and viral envelope proteins (32). Following synthesis of the capsid protein (31), the viral genome (1) is encapsidated (13) to form a nucleocapsid (17). Envelope proteins (32) are co-translationally inserted in the secretory pathway (16) of the cell (3) before reaching the plasma membrane (15). Envelope proteins are post-translationally modified along the secretory pathway (16). Then, the nucleocapsid (17) and viral envelope proteins (32) bound to the cell membrane (15) are assembled and a viral particle (20) is released (21).

Figure 2:
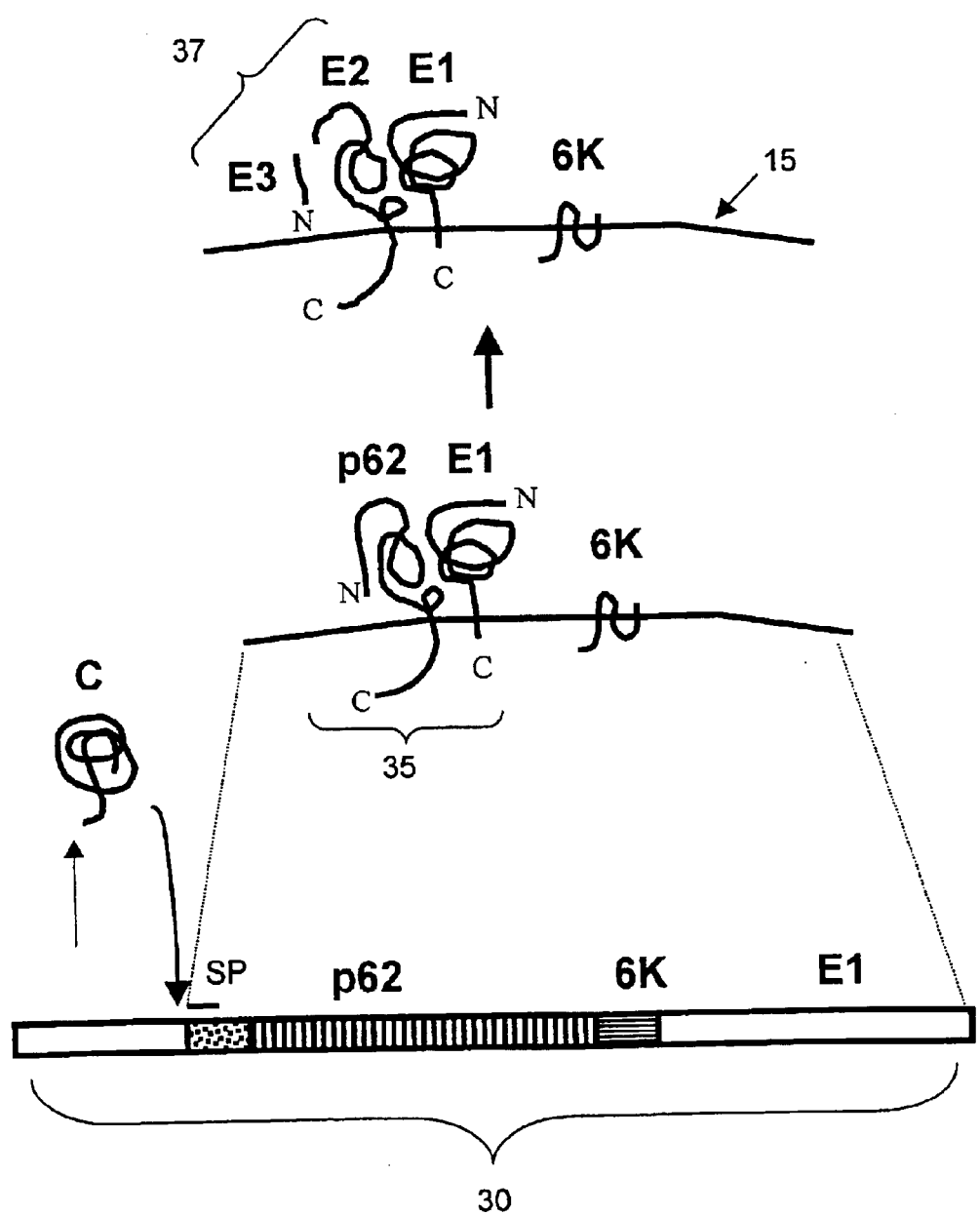
FIG. 2 schematizes the biosynthesis of Sindbis structural proteins.

FIG. 2 shows with more detail the biosynthesis of the viral structural proteins. The structural proteins, namely proteins C, p62, 6K, and E1, are sequentially translated and processed from a common polyprotein precursor (30). In order to form a nucleocapsid, the C protein encapsidates the viral RNA via interaction with the N-terminal positively charged portion of the protein. Autoproteolysis of the C protein from the polyprotein precursor (30) unmasks a signal peptide (SP) at the N-terminus of the p62 protein, thereby directing the nascent envelope proteins to the secretory pathway. p62 and E1 heterodimerize (35) in the endoplasmic reticulum 20 to 30 minutes after their synthesis. p62 is cleaved at a dibasic site in the trans Golgi to produce membrane-anchored E2 and associated E3 (37). The E3 protein is not found in the virion but is essential for transport of the envelope proteins to the cell surface (15). Assembly of the viral particle is driven by interaction of the nucleocapsid and the cytoplasmic tail of the E2 envelope protein.

More preferably, the viral genome or a part thereof is incorporated into a vector such as a bacterial plasmid (e.g. pBluescript KS II, pGEM-7zf) in order to facilitate the insertion of exogenous nucleic acids and the modification of the viral genome. In one embodiment, the plasmid comprises an origin of replication and a sequence encoding β-lactamase so as to select bacterial colonies containing said plasmid when grown on plates containing ampicillin. The viral genome is incorporated into cloning sites present in the plasmid. Plasmid DNA can be prepared and purified using standard procedures (e.g. alkaline lysis followed by ion-exchange chromatography). According to an embodiment of the present invention, exogenous nucleic acids are cloned into the Sindbis genome, itself incorporated into a plasmid.

In the case of the Sindbis genome or other alphaviral genomes, it is highly preferable that the plasmid contain a DNA-dependent RNA polymerase promoter (e.g. pBluescript KS II containing a T7 RNA polymerase promoter or pGEM7zf containing a SP6 RNA polymerase promoter). It is then easier to synthesized in vitro RNA copies of the viral genome before transfecting these RNA copies in host cells. Furthermore, it is highly preferable that the alphaviral genome be cloned such that the RNA polymerase initiates transcription on the plasmid template at the first nucleotide of the alphaviral genome.

It is well known in the art how to synthesize in vitro RNA copies of viral genomes such as the Sindbis genome. Typically, DNA molecules complementary to the Sindbis genomic RNA are synthesized and cloned into a bacterial plasmid vector immediately 3' to a DNA-dependent RNA polymerase promoter (e.g. SP6, T7). A vector that contains the Sindbis genome is linearized at a unique restriction site introduced at the 3' end of the cDNA copy of the Sindbis genome. In vitro transcription of the Sindbis genome is then performed using a DNA-dependent RNA polymerase (e.g. SP6, T7) according to standard protocols. The in vitro synthesized copies of the Sindbis genome can be transfected into cells according to standard protocols.

It is also well known in the art how to modify a viral genome contained in a bacterial plasmid vector using standard recombinant DNA technology. It is also known that the Sindbis genome can accommodate two subgenomic promoters to initiate transcription of two nucleic acids from a single copy of the viral genome. The examples given hereinafter rely on the presence of two active subgenomic promoters within a modified Sindbis genome. Furthermore, according to the present invention, exogenous nucleic acids are inserted into a viral genome and are operatively linked to a subgenomic promoter. Therefore, the viral genome must comprise at least one cloning site downstream of said subgenomic promoter. Preferably, the viral genome is modified so as to comprise a plurality of such cloning sites in order to insert exogenous nucleic acids in a given orientation dictated by the order of the cloning sites. The possibility of inserting exogenous nucleic acids (e.g. cDNAs or cDNA fragments) that keep their natural orientation with respect to the initiation of transcription is advantageous in a screening system because it decreases by a factor of two the number of exogenous nucleic acids that must be screened.

In one of the enclosed examples (Example 1), the Sindbis genome has been modified to allow the rapid identification of nucleic acids encoding a signal peptide. The modification is based on the inactivation of an essential viral signal peptide.

In another one of the enclosed examples (Example 2), the Sindbis genome has been modified so as to allow the rapid identification of nucleic acids encoding either proteases or proteins which somehow trigger a proteolytic activity. The modification is based on the fact that production of viral particles can be inhibited by fusion of a fetter protein to one of the structural proteins such that the latter are no longer capable of efficiently forming viral particles.

In yet another of the enclosed examples (Example 3), the Sindbis genome has been modified to allow the selection of nucleic acids encoding drug-resistance proteins or peptides. The modification of the viral genome is such that viral particles are produced only if an exogenous nucleic acid, encoding or triggering the activation of a cellular activity capable of inactivating the suppressive property of the drug, is inserted into the viral genome.

ii) Suppressive Conditions

In theory, production of viral particles can be blocked by impairing any essential function of non-structural and/or structural proteins. However, it is understood that impairment of the function of non-structural proteins will likely inhibit self replication of the viral genome and/or transcription from a subgenomic promoter, thereby preventing expression of exogenous nucleic acids inserted in the viral genome. According to the present invention, production of viral particles is suppressed or attenuated by impairing the normal function of structural proteins. The suppressive condition can interfere with the production of viral particles in various ways, including, but not limited to, the following.

1. it disrupts assembly of capsid proteins and viral genome;
2. it disrupts assembly of nucleocapsid with the cytosolic tail of p62;
3. it changes the subcellular localization of structural proteins;
4. it disrupts the heterodimerization of envelope proteins;
5. it disrupts the infectivity of the released viral particles.

As will be explained hereinafter, the suppressive condition is more preferably a mutation introduced in the coding sequence of the structural virus proteins. However, it is also conceivable to use a substance inhibiting specifically viral packaging functions, as will be explained in more detail hereinafter.

It is understood that the activity being impaired by a suppressive condition should be restored in some way by expression of an appropriate exogenous nucleic acid. Production of viral particles is thus indicative that the suppressive condition has been overcome and that the exogenous nucleic acid inserted into the viral genome is a nucleic acid having a desired feature or encoding a desired function. Thus, the suppressive condition is designed according to the feature or function that is desired.

In one embodiment of the present invention, a dysfunctional viral genome is engineered by mutating the signal peptide of the p62 protein such that production of viral particles is dependent on the expression of a functional signal peptide provided by an exogenous nucleic acid (see Example 1). In another embodiment of the invention, a dysfunctional viral genome is engineered by fusing a fetter protein to a structural protein (see Example 2). Generation of other dysfunctional viral genomes is well within the knowledge of the skilled artisan by using routine experimentation. The person skilled in the art will understand that various suppressive conditions may be used, the suppressive condition being selected according to the feature which is desired for the exogenous nucleic acid.

iii) Insertion of Exogenous Nucleic Acids in the Viral Genome and Production of Libraries of Recombinant Viral Genomes Containing Exogenous Nucleic Acids The exogenous nucleic acid may be derived from any source, i.e. any organism, tissue or cell type, disease state, etc. In one embodiment of the invention, a plurality of different nucleic acids is inserted into a plurality of copies of a viral genome to provide a plurality of recombinant viral genomes each expressing a unique exogenous nucleic acid and/or encoding a unique protein or peptide. Alternatively, one known or unknown nucleic acid of interest encoding one particular exogenous protein or peptide may be inserted into the viral genome.

Preferably, the exogenous nucleic acid is derived from a nucleic acid library and a plurality of exogenous nucleic acids are inserted into copies of the viral genome to yield a pool of recombinant viral genomes. The library may be obtained from a tissue or a cell type of interest or synthesized artificially. This library may be a cDNA library, genomic library, an RNA library, an expressed sequence tag library, a library made of randomized artificial sequences, or any other kind of library comprising nucleic acids from any kind of organism, tissue, or cell type known to the skilled artisan. Preferably the library is derived from a mammalian source. However, the library may also be derived from reptilian, amphibian, avian, insect, plant, fungi, bacterial cells, etc. In some instance, the nucleic acid library will be derived from a subtractive library, for example a library which comprises cDNAs differently expressed in a disease state when compared to the corresponding healthy tissue. Suitable nucleic acid libraries may be generated using standard methods (see for example Sambrook et al., *Molecular Cloning: A Laboratory Manual*, $2^{nd}$ Ed. Cold Spring Harbor (1989)). Alternatively, a suitable library may be obtained from numerous commercial sources, including but not limited to Clontech (Palo Alto, Calif.), Stratagene (La Jolla, Calif.) and Phenogene Therapeutics (Montreal, QC, Canada).

Alternatively, the exogenous nucleic acid may be derived from mRNA isolated from a tissue or cell type of interest. In this case, the mRNA would be purified and reverse transcribed into cDNA using methods well known in the art. Although exogenous nucleic acids of any type can be screened and selected using the present invention, examples given below rely on cDNA or fragments of cDNA as a source of exogenous nucleic acids. In these examples, cDNAs are obtained using standard methods. Fragments of cDNAs are generated by partial digestion of cDNAs with restriction enzymes (e.g. Sau3A, RsaI). cDNAs or fragments of cDNAs may contain a translation start codon (e.g. ATG). Alternatively, a translation start codon may be provided by the viral genome by modifying the genome so as to place a translation start codon upstream of the cloning sites for the exogenous nucleic acid.

The exogenous nucleic acids are cloned into the Sindbis viral genome cloning site to produce recombinant viral genomes. As stated previously, it is advantageous to incorporate the viral genome into a plasmid. According to this embodiment, exogenous nucleic acids are cloned into recombinant plasmids having incorporated a copy of the viral genome. The resulting population of plasmids is transformed in *Escherichia coli* by electroporation according to standard procedures. A typical yield is $1 \times 10^5$ transformants/ $\mu$g of starting mRNA. A person skilled in the art will understand that the required number of individual transformants depends on the predicted abundance of exogenous nucleic acids having the desired feature within the starting population of exogenous nucleic acids. Plasmids may be prepared and purified according to standard procedures. RNA copies of the recombinant viral genomes containing exogenous nucleic acids may be synthesized according to known methods as will be explained in more detail hereinafter.

iv) Insertion of the Recombinant Viral Genome into a Suitable Host and Conditional Assembly of Viral Particles Production of viral particles requires the availability of certain molecular components. As for any virus, the infected host provides components to allow the replication of the viral genome, the expression viral proteins, and finally, the assembly and the released of viral particles. However, according to the present invention, the availability of some of these components is dependent on insertion of an exogenous nucleic acid of interest into the viral genome.

When using a viral genome derived from single-stranded RNA viruses, the recombinant viral genome would be inserted into the host cell in a RNA form. However, when using a viral genome derived from DNA viruses, the recombinant viral genome would be inserted into the host cell in a DNA form. Introduction of the recombinant viral genome into eukaryotic host cells can be carried out using a number of different well known procedures. Transfection with electroporation, lipofection, precipitate uptake, and microinjection are some of the available techniques to introduce nucleic acids into animal cells. In the preferred embodiments disclosed herein, the host is a mammalian cell line, namely the BHK-21 cell line.

Examples of transfection of BHK-21 cells with modified Sindbis genome by electroporation are given. Control experiments have shown that, in the case of viral genomes able to produce infectious viral particles, about 50% of transfected cells have given rise to viral plaques by 16 hours post-transfection, as evidenced by the presence of groups of 5–20 neighboring cells expressing the viral capsid protein detected by immunofluorescence. Therefore, when performing expression screening using modified Sindbis viral genome, it is usually preferable to change the cell culture medium 16 hours after transfection and leave the medium on the cells to accumulate viral particles for 3 hours.

v) Isolation of the Recombinant Viral Particles and Identification of the Exogenous Nucleic Acids Inserted Therein Once produced, viral particles can be collected from the culture medium and propagated. Alternatively, viral particles can be collected from within the host by cell lysis.

Preferably, the viral genome is capable of autoreplication and recombinant Sindbis particles produced thereof are infectious. These properties allow for the propagation of the viral particles containing the exogenous nucleic acids having the desired feature. The amplification of the recombinant viral genome that is thereby afforded increases greatly the sensitivity of the screening method. However, autoreplication and/or infectiousness is not compulsory since, theoretically, it is possible to isolate a single viral particle using very sensitive techniques.

According to a preferred embodiment, propagation of viral particles is performed as follows. Medium containing viral particles is left on "naive" BHK-21 cells for 1 to 3 hours to allow binding and internalization. The medium is then changed and cells are further incubated, typically for 16 hours, to allow replication of the viral genome and de novo production of viral particles. In the case of recombinant RNA viruses (e.g. recombinant alphaviruses, recombinant Sindbis), total RNA is extracted from the cells and the content of the modified viral genomes is identified as described below. In the case of recombinant DNA viruses, DNA is extracted from the cells and the content of the modified viral genomes is identified using a PCR reaction as described below.

If required, propagation can be repeated to amplify the signal. However, it is understood that numerous passages of the initial population of viral particles may select for a subpopulation of viral particles, thereby introducing a bias in the results of the screening process.

Alternatively, the viral particles can be directly purified from the medium of transfected cells instead of being propagated. Purification is done according to published procedures, e.g. by heparin-agarose affinity chromatography for recombinant Sindbis viral particles.

Once recombinant viral particles comprising an exogenous nucleic acid having a desired property have been isolated and/or propagated, it is generally desirable to identify and/or characterize the exogenous nucleic acids inserted in the viral genome contained within the viral particles. This can be performed in various ways which are within the knowledge of a person skilled in the art. The examples hereinafter provide some ways to do so in the case of a RNA virus. Specifically, RNA extracted from viral particles or from cells infected with viral particles is reversed transcribed using a RNA-dependent DNA polymerase and a primer 3' to the cloning site(s) for the exogenous nucleic acid. The resulting first strand cDNA is used as a template in a polymerase chain reaction (PCR) using a primer 5' to cloning site of the exogenous nucleic acid and a primer 3' to the cloning site(s) for the exogenous nucleic acid. To increase sensitivity, the reverse transcription can be coupled with the PCR reaction in a one-step RT-PCR. In this case, both 5' and 3' primers can be included in the reaction. Products of the RT-PCR reaction can be: i) cloned in a bacterial plasmid (e.g. pBluescript KS II+) and sequenced; ii) analyzed by digestion with restriction enzymes followed by gel electrophoresis; iii) used as hybridization probe(s) in expression profiling or microarray analysis; iv) otherwise characterized.

Sequence comparisons with known polynucleotide sequences in databases may confirm the function of the isolated exogenous nucleic acid and/or reveal homologies with nucleic acids encoding known functions.

v) Applications of the Identified Exogenous Nucleic Acids Having a Desired Property The exogenous nucleic acids selected and identified according to the method of the invention as well as the peptides and proteins encoded by the same may have many uses. They may be useful for research applications and laboratory use. For instance, they may be used for further screening procedures e.g. as a library, they may serve as probes for the discovery and isolation of various genes and/or diseases, be used for the production of antibodies, be used for the development and the use of oligonucleotide or oligoribonucleotide sequences antisense DNA or RNA molecules or ribozymes. Some of the genes and gene products identified and isolated by the method of the present invention may directly be used as therapeutic agents or, alternatively, as therapeutic targets. These applications and others are known in the art as well as the manner in which they can be reduced to practice.

D) Nucleic Acid Molecule Encoding a Dysfunctional Viral Genome and Kit for Using the Same The invention also relates to an isolated nucleic acid molecule encoding a dysfunctional viral genome wherein the production of a viral particle using this nucleic acid molecule is dependent on insertion therein of an exogenous nucleic acid having a desired feature. Preferably, the dysfunctional viral genome comprises a nucleic acid encoding a dysfunctional viral structural protein and the production of a viral particle is dependent on the expression of a functional viral structural protein. The exogenous nucleic acid having a desired feature is preferably selected from the group consisting of nucleic acids encoding a signal peptide, nucleic acids encoding at least partially for a protein having a signal peptide, nucleic acids encoding proteases, nucleic acids encoding proteins or peptides having a proteolytic activity and nucleic acid encoding drug-resistance proteins or peptides. According to a most preferred embodiment the viral genome encodes for Sindbis virus and the nucleic acid is incorporated into a plasmid vector.

The invention also encompasses kit for selecting a nucleic acid having a desired feature. Such kit comprises:

a nucleic acid molecule encoding a dysfunctional viral genome as the one described hereinbefore; and at least one element selected from the group consisting of instructions for using said kit, reaction buffer(s), enzyme(s), probe(s) and pool(s) of exogenous nucleic acids.

The methods for producing such kit are well within the knowledge of those skilled in the art.

EXAMPLES

As it will now be demonstrated by way of examples hereinafter, the invention provides a very rapid, efficient and accurate method to select a particular nucleic acid having a desired feature. Example 1 gives an example of how to select a nucleic acid encoding a signal peptide, a secreted protein or a membrane protein; Example 2 gives an hypothetical example of how to select a nucleic acid encoding a protease, and Example 3 gives an hypothetical example of how to select a nucleic acid encoding a drug-resistance protein. In these examples, the suppressive condition is obtained by modifying the viral genome so as to: 1) affect entry of envelope proteins in the secretory pathway (Example 1); 2) affect normal function(s) of the capsid protein (Example 2); and 3) inhibit or suppress specifically viral packaging function(s) (Example 3). Although any methods and materials similar or equivalent to those described herein can be used in the practice or testing of the present invention, the preferred methods and materials are described.

A) Materials and Methods

The following are experimental procedures and materials that were used for the examples set forth below.

Enzymes and Reagents

Restriction enzymes and DNA-modifying enzymes were purchased from New England Biolabs (Cambridge, Mass.) unless otherwise stated. Titan™ one-tube RT-PCR system was purchased from Roche Molecular (Laval, Quebec, Canada). Taq DNA polymerase was purchased from Amersham Pharmacia Biotech (Baie d'Urfé, Quebec, Canada). Synthetic oligonucleotides were obtained either from Hukabel Ltd. (Montreal, Quebec, Canada), Life Technologies (Burlington, Ontario, Canada) or MWG Biotech Inc. (High Point, N.C.). Cell culture reagents were from Life Technologies unless otherwise stated.

Cell Culture and Transfection

BHK-21 cells (ATCC no. CCL-10, purchased from Invitrogen Corp., Carlsbad, Calif.) are grown in alpha minimal essential medium supplemented with 0.29 mg/ml L-glutamine, ribonucleosides and deoxyribonucleosides (10 $\mu$g/ml) and 5% (v/v) fetal bovine serum, 100 U/ml penicillin, 100 mg/ml streptomycin (referred hereafter as complete medium). Cells are passaged when reaching 80–95% confluence by incubating with 0.05% (v/v) trypsin/0.5 mM EDTA (Wisent Inc., St-Bruno, QC, Canada). Lipofection is performed as follows. Lipid-DNA complexes (containing typically 1–2 µg of DNA) are formed using the FuGENE-6™ reagent (Roche Molecular; Laval, Quebec, Canada) according to the manufacturer's instructions. Cells are transfected the day after plating (typically 10,000 cells/cm$^2$) by adding the lipid-DNA complex to the culture medium. After a 3 hour incubation, the medium is changed and cells are usually processed after 48 hours. Electroporation is performed as follows. Exponentially-growing cells are trypsinized as described above and washed twice in phosphate buffered saline (PBS; 137 mM NaCl, 2.7 mM KCl, 10 mM Na$_2$HPO$_4$, 1.8 mM KH$_2$PO$_4$, pH 7.4). Cells are resuspended in PBS at a concentration of 10$^7$/ml. Four µg of RNA is added to 0.5 ml of the cell suspension in a 0.4 cm electroporation cuvette (Bio-Rad; Mississauga, Ontario, Canada). Cells are electroporated once with a GENE PULSER II™ unit (Bio-Rad) set at 1.25 kV, 25 µF and maximal resistance. The electroporated cell suspension is then added to 10 ml of complete medium and plated, typically in one 100 mm petri dish or in five 60 mm petri dishes.

Production of Recombinant Proteins and Polyclonal Antibodies

Capsid Protein

The capsid protein coding sequence is amplified by 25 cycles of PCR using 5 ng of DH-BB (Invitrogen, Carlsbad, Calif.) as template, 25 pmoles of oligonucleotide 24-1V (5'-ggatccaatagaggattctttaac-3'; SEQ ID NO: 1) as forward primer, 25 pmoles of oligonucleotide 21-2V (5'-tcaccactcttctgtcccttc-3'; SEQ ID NO:2) as reverse primer, 200 µM of deoxynucleotides, 1.25 U of Pwo DNA polymerase, 1×buffer supplied by the manufacturer (Roche Molecular; Laval, Quebec, Canada) in a total volume of 50 µl. Cycling conditions were 1 minute at 94° C., 1 minute at 50° C. and 1.5 minutes at 72° C. The resulting 795 bp PCR fragment was cloned in the EcoRV site of pBLUESCRIPT KS™ (Stratagene, La Jolla, Calif.). This construct was then digested with HindIII and BamHI and the capsid sequence-containing fragment was purified and cloned into plasmid pQE30 digested with HindIII and BamHI. pQE30 (Qiagen, Mississauga, Ontario, Canada) contains an origin of replication, the β-lactamase coding sequence, and the taq promoter controlling the expression of a given fusion protein containing 6 histidines at its N-terminus. The hexahistidine tag coordinates nickel atom, thereby allowing purification of the fusion protein by metal affinity chromatography. pQE30 containing the capsid coding sequence described above is transformed in strain SG13009[pREP4]. The fusion protein is produced and purified under denaturing conditions (6M guanidine hydrochloride, 200 mM NaCl, 100 mM sodium phosphate, 10 mM Tris pH 8.0, 2 mM imidazole, 5 mM β-mercaptoethanol) according to the manufacturer's instructions (QIAEXPRESSIONIST™ kit, Qiagen, Mississauga, Ontario, Canada). The protein is further purified after electrophoresis on denaturing polyacrylamide gel. The protein is extracted from the gel by incubation in bicarbonate buffer (50 mM NH$_4$HCO$_3$; 0.1% SDS) followed by precipitation with trichloroacetic acid (10% v/v). The precipitate is resuspended in 8 M urea and dialyzed at 4° C. against 4 liters of TBS.

E1 Protein

The E1 protein coding sequence is amplified by 25 cycles of PCR using 5 ng of DH-BB (Invitrogen, Carlsbad, Calif.) as template, 25 pmoles of oligonucleotide 25-2V (5'-ggatcctacgaacatgcgaccactg-3'; SEQ ID NO:3) as forward primer, 25 pmoles of oligonucleotide 21-3V (5'-tcatcttcgtgtgctagtcag-3'; SEQ ID NO:4) as reverse primer, 200 µM deoxynucleotides, 2.5 U of Pwo DNA polymerase, 1×buffer supplied by the manufacturer (Roche Molecular; Laval, Quebec, Canada) in a total volume of 50 µl. Cycling conditions were 1 minute at 94° C., 1 minute at 57° C. and 1.5 minutes at 72° C. The resulting 1320 bp PCR product is cloned into pQE30 as described for the capsid protein fragment. The resulting construct is digested with StuI and HindIII, blunted and recirculized. pQE30 containing the sequence encoding amino acids 1 to 340 of E1 is transformed in strain SG13009[pREP4]. The fusion protein is produced and purified under denaturing conditions as for the capsid protein.

Polyclonal Antibodies

200 µg of recombinant protein mixed with complete Freund's adjuvant (VWR Canlab, Montreal, Quebec, Canada) is injected subcutaneously to New Zealand White rabbit on day 1. On days 15 and 28, another 100 µg of recombinant protein mixed with incomplete Freund's adjuvant is similarly injected. Rabbits are bled 7 days after the last injection.

Immunofluorescence

Except for incubation with primary antibodies done at 4° C., all washes and treatment of fixed cells are done at room temperature. Cells are rinsed with PBS and fixed with 2% (w/v) paraformaldehyde in PBS. Cells are washed with PBS. For detection of the cytoplasmic capsid protein, cells are permeabilized by incubation in 0.1% TRITON X-100™ in PBS for 4 minutes and washed twice with PBS. Cells are then incubated in 50 mM NH$_4$Cl in PBS for 10 minutes at room temperature and washed with PBS. Cells are incubated in PBS supplemented with 0.1% (w/v) bovine serum albumin fraction V and 2% (w/v) dried milk for 3 hours. Cells are then incubated overnight with primary antisera diluted 1/50–1/200 in PBS supplemented with 0.1% (w/v) bovine serum albumin and 0.5% (w/v) dried milk. Cells are washed twice with PBS and incubated for 1 hour in 1/200 dilution of goat anti-rabbit coupled to fluorescein isothiocyanate (BioSource International, Amarillo, Calif.) or tetramethyl rhodamine isothiocyanate (Sigma Chemicals, St.Louis, Mo.) in PBS supplemented with 0.1% (w/v) bovine serum albumin. Cells are washed twice and observed by fluorescence microscopy.

Detection of E1 Protein

Cells are rinsed with PBS. Cell surface proteins are biotinylated with sulfo-NHS-biotin (Pierce, Rockford, Ill.) at 50 µg/ml in PBS supplemented with 1 mM CaCl$_2$ and 1 mM MgCl$_2$ (PBS-CM) for 20 minutes on ice. Cells are washed twice with PBS-CM supplemented with 50 mM NH$_4$Cl. Membrane proteins are solubilized with 0.4 ml of 50 mM Tris-Cl pH 8.0, 150 mM NaCl, 2 mM EDTA, 1% IGEPAL-630™, 0.1% sodium dodecyl sulfate. Cell debris and insoluble material are pelleted by centrifugation at 12,000 g for 5 minutes at 4° C. An aliquot of the supernatant (40 µl) is taken to determine total cellular E1 protein. The remainder is incubated with 10 µl of streptavidin-agarose beads (Pierce, Rockford, Ill.) for 3 hours at 4° C. Beads are pelleted by brief centrifugation and washed twice with PBS. Bound proteins are eluted by boiling the beads for 5 minutes in the following solution: 50 mM Tris-HCl, pH 6.8, 100 mM dithiothreitol, 2% sodium dodecyl sulfate, 0.1% bromophenol blue, 10% glycerol. Proteins are electrophoresed on denaturing polyacrylamide gel and transferred to 0.22 µm nitrocellulose according to standard Western protocols. The nitrocellulose membrane is incubated overnight in Tris-buffered saline (TBS; 25 mM Tris-HCl, pH 7.4, 137 mM NaCl, 2.7 mM KCl) supplemented with 5% (w/v) dried milk and 0.1% (v/v) TWEEN-20™ (Sigma, St.Louis, Mo.). It is then incubated for 3 hours at room temperature with affinity-purified antibody to E1 at a concentration of 1 µg/ml in TBS supplemented with 0.1% (w/v) dried milk and 0.1% (v/v) TWEEN-20™. The membrane is washed twice with TBS supplemented with 0.1% (v/v) TWEEN-20™. It is then incubated for 1 hour at room temperature with goat anti-rabbit coupled to horseradish peroxidase (Sigma, St.Louis, Mo.) diluted 1/10,000 in TBS supplemented with 0.1% (v/v) TWEEN-20™. The membrane is washed twice with TBS supplemented with 0.1% (v/v) TWEEN-20™. Detection of the protein bound to the antibody complex is performed with the ECL™ reagent according to the manufacturer's instructions (Amersham Pharmacia Biotech, Baie d'Urfé, Canada).

In vitro Transcription

Plasmids (10 µg) containing the SP6 promoter followed by a modified viral genome are linearized, typically with PacI or SwaI. The reaction is then treated for 30 minutes at 56° C. with proteinase K (Roche Molecular, Laval, Quebec, Canada) at 0.2 µg/ml in a buffer containing 10 mM Tris-HCl, pH 7.8, 5 mM EDTA, 0.5% SDS. Linearized plasmid DNA is purified by two phenol:chloroform:isoamyl alcohol (25:24:1) extractions, precipitated, and resuspended in diethylpyrocarbonate-treated water. The in vitro transcription reaction is assembled using components of the RIBOMAX SP6™ kit according to the manufacturer's instructions (Promega, Madison, Wis.) and incubated at 30° C. for 3 hours. RNA is purified with the RNEASY™ kit according to the manufacturer's instructions (Qiagen, Mississauga, Ontario, Calif.). The concentration is determined by spectrophotometry.

RNA Extraction and RT-PCR

Total RNA is purified either by the guanidium isothiocyanate/acid phenol method or using the RNEASY™ kit according to the manufacturer's instructions (Qiagen). 50–500 ng of total RNA is analyzed by RT-PCR using the Titan™ one tube RT-PCR system according to the manufacturer's instructions (Roche Molecular, Laval, Quebec, Canada). Cycling conditions are as follows: 94° C. for 1 minute, 56° C. for 1 minute, 68° C. for 1 minute.

B) EXAMPLE 1

Figure 3A:
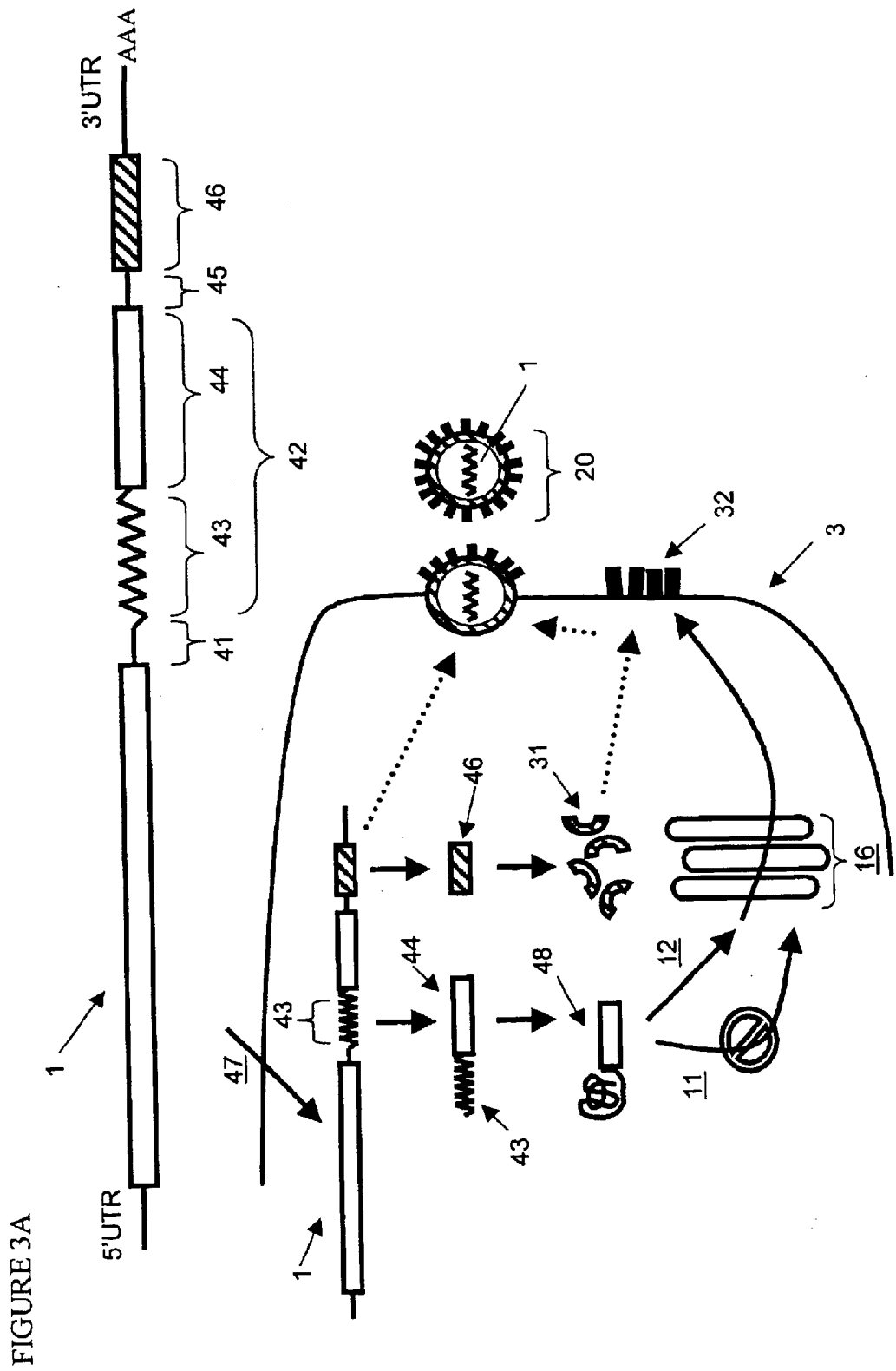
FIG. 3A schematizes a modified viral genome and a method for using the same in order to select an exogenous nucleic acid encoding a signal peptide.

Selection of Nucleic Acids Encoding a Signal Peptide or Proteins Having a Signal Peptide i) Background and Strategy Secreted and membrane-bound proteins are among the most important class of drug targets since they are key players in processes affected in diseases such as hormone/growth factor response and cell-cell adhesion. Secreted and membrane-bound proteins are synthesized as precursors and these are characterized by a short N-terminal sequence ("the signal peptide") which serves to direct the precursor to the cellular secretory pathway and mediate translocation of the nascent polypeptide chain across the lipid bilayer. Because of their great therapeutic potential, great efforts are deployed to identify genes encoding secreted and membrane-bound proteins. In the present example, the Sindbis genome has been modified so as to allow the rapid identification of nucleic acids encoding signal peptides. The modification is based on the inactivation of an essential signal peptide. More specifically, this example demonstrates that the signal peptide of p62 can be mutated, thereby impairing entry of envelope proteins in the secretory pathway of the cell. Screening is conducted according to the principle of a so-called "signal trap", meaning fragments of cDNAs are fused to the mutated p62 protein and only those encoding a signal peptide in frame with mutated p62 can restore the membrane localization of the envelope proteins, thereby leading to selection of said fragments. Methods relying on a signal trap to identify secreted proteins are known in the art (Tashiro et al., 1993), but none of these methods has been adapted to the production of viral particles.

As shown in FIG. 3A, according to a preferred embodiment of the invention, the modified Sindbis virus genome (1) comprises a first subgenomic promoter (41) which corresponds to the naturally occurring sequence truncated 5 nucleotides after the site of initiation of transcription. It also comprises a second subgenomic promoter (45) which corresponds to 46 nucleotides upstream and 14 nucleotides downstream of the site of initiation of transcription. The first subgenomic promoter (41) serves to express a messenger (42) consisting of an exogenous nucleic acid (43) inserted into the viral genome and fused to the coding sequence of the envelope proteins precursor whose signal peptide has been rendered dysfunctional by mutagenesis (44). The second subgenomic promoter (45) serves to express a sequence (46) encoding the capsid protein (31). Upon transfection (47) in a suitable host (3), only recombinant Sindbis genome (1) comprising an exogenous nucleic acid (43) encoding a functional signal peptide fused to a dysfunctional envelope proteins (48) will result in the production of recombinant viral particles (20) since only such exogenous nucleic acids (43) will be capable of restoring the entry (12) of the envelope proteins in the secretory pathway (16). On the contrary, recombinant Sindbis genome (1) comprising an exogenous nucleic acid (43) not encoding a functional signal peptide will not be capable (11) of restoring the entry of the envelope proteins in the secretory pathway (16) and will not lead to production of viral particles.

ii) Plasmid Construction

The general process of plasmid construction is schematized on FIGS. 4A to 4D. For simplification purposes, some of the cloning intermediates are not described or depicted. Similarly, only the restriction sites relevant to the cloning are shown and DNA fragments are not necessarily drawn to scale.

The mouse growth hormone mRNA was isolated by RT-PCR (401) using total RNA extracted from mouse pituitary (400) and forward primer 30-1 Y (5'agcgaattcgtcctgtggacagatcactgc-3'; SEQ ID NO: 5) and reverse primer 30-2Y (5'gctctcgaggaaggcacagctgctttccac-3'; SEQ ID NO:6). The 736 nt RT-PCR product was digested by EcoRl and XhoI and cloned in plasmid pCDNA1.1 (Invitrogen, Carlsbad, Calif.) that had been digested by EcoRl and XhoI (402). The resulting construct was designated VB-P1 (403). Part of the envelope proteins precursor was amplified from plasmid DH-BB (Invitrogen, Carlsbad, Calif.). using forward primer 30-20V (5'cttctcgagcagtttaaacgtgagcttccc-3'; SEQ ID NO:7) and reverse primer 30-16V (5'acgtctagatcatcttcgtgtgctagtcag-3'); SEQ ID NO:8) (404). The resulting PCR product encoded the p62 envelope protein minus the first 13 amino acids (p62d13), the 6K peptide (6K) and the E1 protein (E1). This product was digested with XhoI and Xbal and cloned in XhoI-Xbal digested plasmid VB-P1 (405). The resulting construct was designed VB173. A double-stranded oligonucleotide consisting of oligonucleotide 47-1V (5'tcgagcagatctgcagcaccactggtcacggcaatgtgtcggagcgg-3'; SEQ ID NO:9) annealed to oligonucleotide 43-2V (5'ccgctccgacacattgccgtgaccagtggtgctgcagatctgc-3'; SEQ ID NO:10) was inserted in XhoI-Pmel digested VB173 to produce VB175 (406). The latter plasmid contained the mutated p62 coding sequence (p62mutRS, i.e. arginine substituted for leucine at position 11 and serine substituted for leucine at position 12). The capsid coding sequence was amplified from DH-BB using forward primer 63-1V (5'gtgtccaagccatcagaggggaaataaagcatctctacggtggtcctaaatag tcagcatagt-3') SEQ ID NO:11) and reverse primer 28-6V (5'ccagagctcatgcggaccactcttctgt-3'; SEQ ID NO:12) (407). The forward primer contains nt −46 to +14 of the Sindbis subgenomic, +1 being the site of initiation of transcription. The reverse primer corresponds to the last 12 nt of the capsid coding sequence preceded by the sequence (5'gagctcatgcgga-3') SEQ ID NO: 33) such that the extremity of the PCR product contains, in addition to the capsid sequence, a serine codon, an alanine codon, a termination codon, and a SacI restriction site. The PCR product was cloned in the unique blunted XbaI site of VB175(408). Plasmid intermediates were constructed such that a sequence comprising the restriction sites for NotI and BamHi was inserted between the EcoRl and XhoI sites of VB188 (409). A NotI-XhoI fragment comprising nt 20–102 of the Keratin-Associated protein (KAP) was cloned in the plasmid from step 409 to produce VB-P2 (410). Insertion of this fragment encoding the first 22 amino acids of KAP will serve as a negative control since they do not encode a signal peptide. Fragments excised from VB188 and VB-P2 using SacI and blunted using T4 DNA polymerase were cloned in the unique PmlI site of VB41 (411). This plasmid was constructed by ligating a blunted SacI-PmlI 772 bp fragment of pSinRep5 in the unique EcoRV site of pCDNA1.1 (both pSinRep5 and pCDNA1.1 purchased from Invitrogen. Carlsbad, Calif.). The resulting plasmids contain a modified viral genome as depicted in FIG. 3A and having inserted an exogenous nucleic acid encoding a signal peptide (VB192, mGH) or not (VB193, KAP). To introduce a unique restriction site after the 3' untranslated region of the Sinbis modified genome, VB193 was digested with HindII and the 5997 bp fragment was circularized to produce VB194 (412). A double-stranded oligonucleotide consisting of oligonucleotide 24-7V (5'-tcgcgatttaaattaattaagctt-3'; SEQ ID NO:13) annealed to oligonucleotide 24-8V (5'-aagcttaattaatttaaatcgcga-3'; SEQ ID NO:14) and comprising the restriction sites for NruI, SwaI, PacI, and HindIII was cloned in the unique and blunted EcoR1 site of VB194 to produce VB195(413). A 4303 bp PmlI-PvuI fragment encompassing this insertion was then subcloned in a PmlI-PvuI fragment of both VB192 and VB193 to produce VB196 and VB197 respectively (depicted only for VB193). In order to be able to directionally clone cDNA fragments at the indicated BamHl site of VB197, additional steps were taken to remove the BamHl site at position 7334 relative to the first nt of the modified viral genome and sites EcoRV at positions 2748 and 6876 relative to the first nt of the modified viral genome. Removal of these sites was done by PCR-based mutagenesis according to standard protocols.

The sequences of important regions of the modified viral genome were verified by DNA sequencing. FIG. 5A to 5E show the nucleotide sequences surrounding the cloning sites for the exogenous nucleic acid (FIG. 5A; SEQ ID NO:21); the nucleotide sequence surrounding the second subgenomic promoter (FIG. 5B; SEQ ID NO:22); the nucleotide sequence surrounding the end of the capsid protein coding sequence (FIG. 5C; SEQ ID NO:23); the nucleotide sequence around the unique SwaI restriction site (FIG. 5D; SEQ ID NO:24); and in FIG. 5E, the nucleotide and amino acid sequences of the wild type (SEQ ID NOS:25 and 26) and mutated p62 signal peptide type (SEQ ID NOS:27 and 28).

iii) Establishment of Suppressive Condition

Figure 8A:
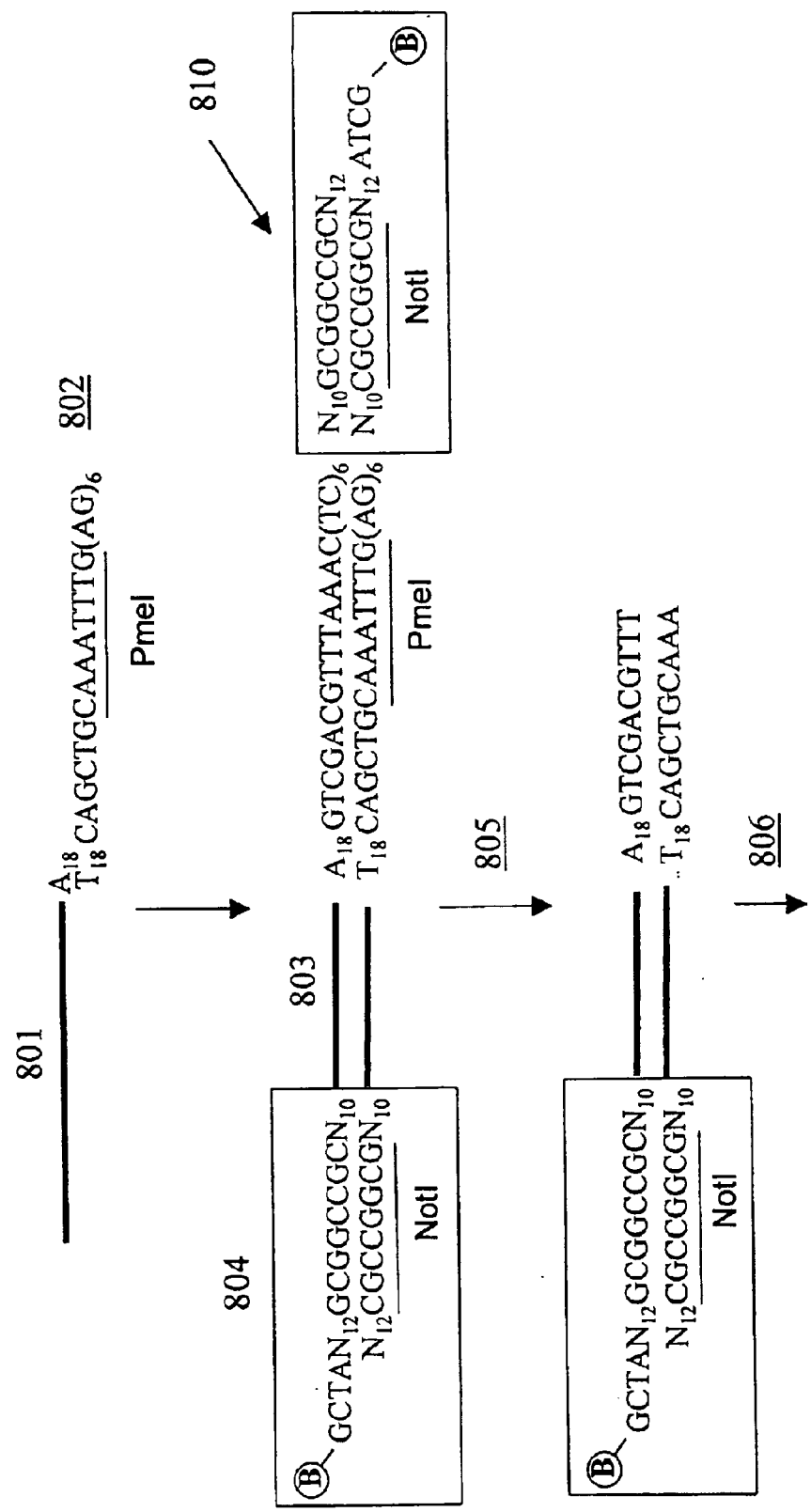
FIGS. 8A and 8B schematize a method to obtain a library enriched in fragments corresponding to the 5' regions of cDNAs FIGS. 9A, 9B and 9C schematize the cloning process of a plasmid containing a modified viral genome used to select an exogenous nucleic acid encoding a protease or a protein that triggers a proteolytic activity.
Figure 8B:
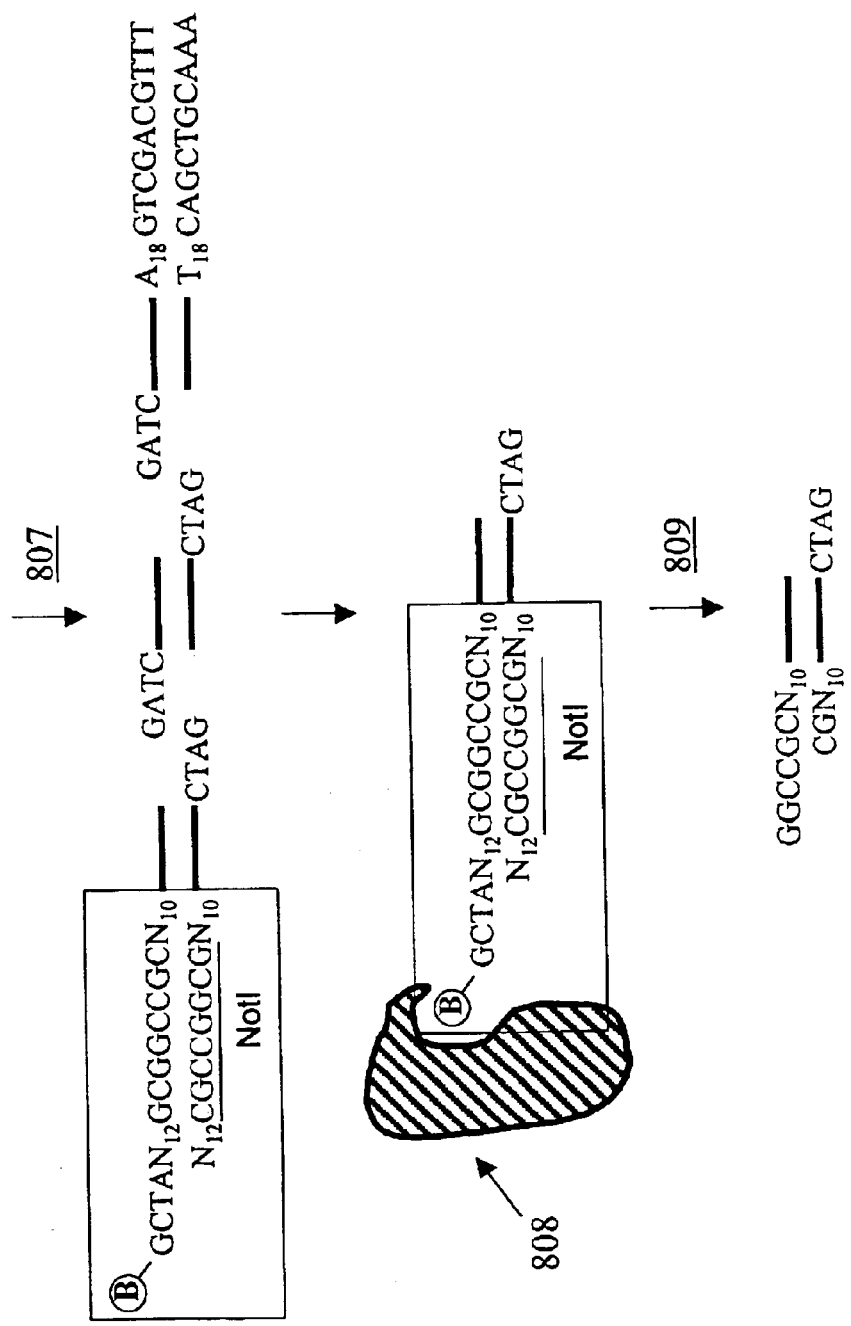

To determine the subcellular localization of envelope proteins, the amount of E1 protein at the cell surface was detected by biotinylation and immunoblotting as described in Materials and Methods. The presence of E1 at the cell surface is indicative of normal biosynthesis of envelope proteins, i.e. entry of p62 and E1 in the secretory pathway, heterodimerization and transport to the cell surface. To prevent entry of p62 in the secretory pathway, we introduced mutations in its signal peptide. These mutations substitutes arginine at position 8 for leucine and serine at position 12 for leucine. When tested in the context of the keratin-associated protein (amino acids 1–22) fused to mutated p62, the mutations introduced in the p62 signal peptide effectively abolish cell surface localization of the E1 envelope protein (FIG. 6, lane KAP-p62mutRS). However, these mutations can be complemented by fusing a secreted protein at the N-terminus of the mutant p62. Indeed, the E1 protein is detected at the cell surface when mouse growth hormone, a secreted protein, is fused to the mutated form of p62 (FIG. 6, lane mGH-p62mutRS). Although not shown, good results were also obtained using an other similar mutated p62 signal peptide (SAAPLVTAMCGSGNVS; SEQ ID NO: 32).

iv) Selection of a Fragment Encoding a Signal Peptide from an Excess of Fragment which Does Not Encode a Signal Peptide To determine the sensitivity of the method of the invention, large quantities of viral genomes not able to produce viral particles were spiked with decreasing amounts of viral genomes able to produce viral particles. In this case, the "negative" viral genome contains the keratin-associated protein fragment fused to mutated p62 protein (transcribed from VB197) whereas the "positive" viral genome contains the mouse growth hormone fused to the mutated p62 protein (transcribed from VB196). The proportion (w/w) of positive to negative viral genomes was 1:10, 1:100, 1:1000, 1:10000, 0:1. The RNA mixture (total of 4 $\mu$g) was transfected in BHK-21 cells, the medium was changed 16 hours later and left to accumulate viral particles for 3 hours. Immunofluorescence analysis indicated that approximately 100,000 cells had been transfected. The medium from transfected cells was incubated on a fresh monolayer of BHK-21 cells for 16 hours to propagate the viral particles. Total RNA was extracted from transfected and infected cells. RT-PCR was performed using oligonucleotides flanking the heterologous nucleic acid fragment (forward primer 18-93V is 5'-agacgcgtagatctcacc-3' (SEQ ID NO:15) and reverse primer 20-13V is 5'-gatccgcaccgcaatatggc-3' (SEQ ID NO:16). As shown in FIG. 7, total RNA from transfected cells always contains modified viral genomes containing the KAP (negative) fragment (FIG. 7, lanes 1–5). The mGH (positive) fragment is detected only at the lowest dilution (FIG. 7, lane 1) presumably because the large excess of KAP-containing viral genome competes efficiently in the other RT-PCR reactions (FIG. 7, lanes 2–5). On the other hand, total RNA from infected cells predominantly contains mGH-containing viral genome (FIG. 7, lanes 7–10). Signal of the latter is detected even when 10,000 times more KAP-containing viral genome is co-transfected (FIG. 7, lane 10). The signal arising from mGH-containing viral genome is amplified by further passage of the initial viral particles population (FIG. 7, lanes 12–15). Molecular weight markers (lambda DNA digested with HindIII and EcoRI) are shown in lanes 6 and 17. The faint signal arising from KAP-containing viral genome in infected cells is due to contaminating cell debris that can be removed by passing the medium on a 0.45 $\mu$m filter before using it to infect a fresh monolayer (not shown). These results demonstrate that a modified viral genome containing a fragment encoding a signal peptide can be retrieved when co-transfected with 10,000 times more modified viral genome containing a fragment which does not encode a signal peptide.

v) Cloning of a Library of Heterologous cDNA Fragments in the Modified Sindbis Replicon The efficiency of screening of genes encoding secreted proteins depends crucially on the input nucleic acid that is fused to the mutated envelope proteins. Indeed, this nucleic acid must minimally encode a signal peptide downstream of an initiator ATG and must not contain a termination codon. Current screening systems use random hexamers to prime messenger RNA for the first strand synthesis of cDNA. After synthesis of the second strand, relatively short fragments (400–800 bp) are selected. The combination of random priming and short cDNAs diminishes the probability of finding a fragment that will encode the signal peptide. A method for the construction of libraries enriched in cDNA fragments corresponding to the 5' extremities of the cDNA was therefore developed. The method involves the addition of tags to the extremities of double stranded ("ds") cDNA, the selective removal of the tag added at the 3' end, the digestion of the modified ds cDNA into smaller fragments and the selection of fragments tagged at their 5' ends. The general strategy is depicted in FIGS. 8A and 8B. The starting RNA is extracted from any organism or species (plant, animal, microorganism) using standard protocols. The mRNA (801) is primed with an oligonucleotide (802; SEQ ID NO: 29) containing, from the 3' to 5', a stretch of thymidine (which typically number 18) that anneal to the poly-adenine tail of the mRNA, a PmeI restriction site and 6 repeats of the dinucleotide GA to minimize degradation by exonuclease. After synthesis and blunting of ds cDNA (803), biotinylated adapters (804) consisting of oligonucleotide 804-1 (5'-Biotin-gctaagcttgctatcggcggccgcgagaattcgt-3'; SEQ ID NO: 30) annealed to oligonucleotide 804-2 (5'-acgaattctcgcggccgccgatagcaagct-3'; SEQ ID NO:31) are ligated to the blunt ends of ds cDNA. Ligation is performed with T4 DNA ligase using a large molar excess of the adapter so that cDNAs are not ligated onto each other. Furthermore, only one end of the adapter is blunt and 5' phosphorylated such that the ligation can proceed only in the desired orientation. Ligation of one molecule of adapter to the end of a cDNA molecule renders the resulting end incompetent for further ligation, thus ensuring that the ends of cDNA are properly modified. After inactivating the ligase by phenol extraction and ethanol precipitation, ds cDNAs are digested (805) with PmeI to remove the biotinylated adapter ligated at the 3' end (810). PmeI recognizes a 8 bp site and is considered a rare cutter in the mammalian genome (approximately 1 site every 80,000 bp). There is thus a very low probability that PmeI will cut inside the cDNA molecule (803). After digestion with PmeI, the cDNA is size-fractionated (806) on a size-exclusion chromatography column (SEPHAROSE CL-2B™, Sigma, St. Louis, Mo.) Fractions containing cDNAs larger than 500 bp are pooled and retained. This step is introduced to remove 1) short cDNAs that arose because of aborted synthesis from the template mRNA, and 2) the excess biotinylated adapter which could interfere with subsequent steps. The cDNAs are then digested (807) either with Sau3A or RsaI, restriction enzymes whose 4 bp recognition site occurs frequently in cDNA. Sau3A leaves BamHI compatible ends whereas RsaI generates blunt ends. The population of cDNA fragments is then incubated with streptavidin-agarose (808) to select biotinylated fragments corresponding to the 5' region of the cDNA. After washes, the bound cDNA fragments are released by digestion with NotI (809), a restriction site present in the biotinylated adapter. Again, NotI is selected because its 8 bp recognition site is very rare in cDNA sequence. Depending on the enzyme used to digest the cDNA, the resulting 5' fragment can be cloned directionally in a vector digested with either NotI and BamHI or NotI and EcoRV.

vi) Screening of a Library of Heterologous cDNA Fragments

A library of NotI-BamHI cDNA fragments was constructed as described above starting from total RNA extracted from mouse embryonic skin at day 16.5 of gestation. These fragments were cloned in an initial vector and amplified by PCR, digested by NotI and XhoI and subcloned into the NotI and XhoI sites of VB197. The size of the library was approximately $2 \times 10^5$ clones. Plasmids were digested with SwaI and RNA copies of the modified viral genomes were transcribed as in Materials and Methods. BHK-21 cells were electroporated with 4 µg of RNA as in Materials and Methods. Cells were plated in a single 100 mm petri dish. The culture medium was changed 16 hours after transfection and left on the cells to accumulate viral particles for 3 hours. Medium containing viral particles was then incubated on 100,000 "naïve" BHK-21 cells for 3 hours to allow binding and internalization. The medium was then changed and cells were further incubated for 16 hours to allow replication of the viral genome and de novo production of viral particles. The propagation steps were repeated once. Total RNA was extracted from the infected cells and the content of the modified viral genomes was amplified by RT-PCR using 500 ng of total RNA, reverse primer 20–13V, forward primer 18–93V, and reagents of the TITAN™ system according to the manufacturer's instructions. Products of the RT-PCR reaction were digested with NotI and XhoI and cloned in pBLUESCRIPT KS II™.

A total of 83 inserts were analyzed by digestion with restriction enzymes and distinct clones were sequenced and compared with known polynucleotide sequences in databases. As shown hereinafter in TABLE 1, only 1 of the 83 inserts did not encode a signal peptide fused in frame with mutated p62 (clone no. 9 in Table 1). The other 82 inserts were represented by eight distinct clones. These 8 clones encoded a signal peptide fused in frame with mutated p62. Three were derived from cDNAs that had not been previously annotated (data not shown). Five clones corresponded to the 5' region of cDNAs known to encode secreted protein (clones nos 1–5 in Table 1).

C) Example 2

Selection of Nucleic Acids Encoding a Protease i) Background and Strategy

Proteases are enzymes which cleave peptide bonds. They are involved in the regulation of important physiological processes such as apoptosis as well as maturation and/or inactivation of bioactive peptides. Proteases represent excellent drug targets since their precise inhibition results in beneficial effects (e.g. to prevent apoptosis or maturation and inactivation of bioactive peptides). In the present example, the Sindbis genome has been modified so as to allow the rapid identification of nucleic acids encoding either proteases or proteins which somehow trigger a proteolytic activity. The modification is based on the fact that production of viral particles can be inhibited by fusion of a fetter protein to one of the structural proteins such that the latter are no longer capable of efficiently forming viral particles. The fetter protein and the structural protein (e.g. capsid) are separated by a peptide sequence known to be cleaved by the protease being screened for the "protease cleavage site". Similar fusion proteins have already described in the art. For instance, Filocamo et al., (1997) and Cho et al. (1997) describes fusion proteins consisting of the hepatitis C virus NS3 protease and the Sindbis capsid protein. However, the use of such fusion proteins for screening exogenous nucleic acids has not been suggested.

Figure 3B:
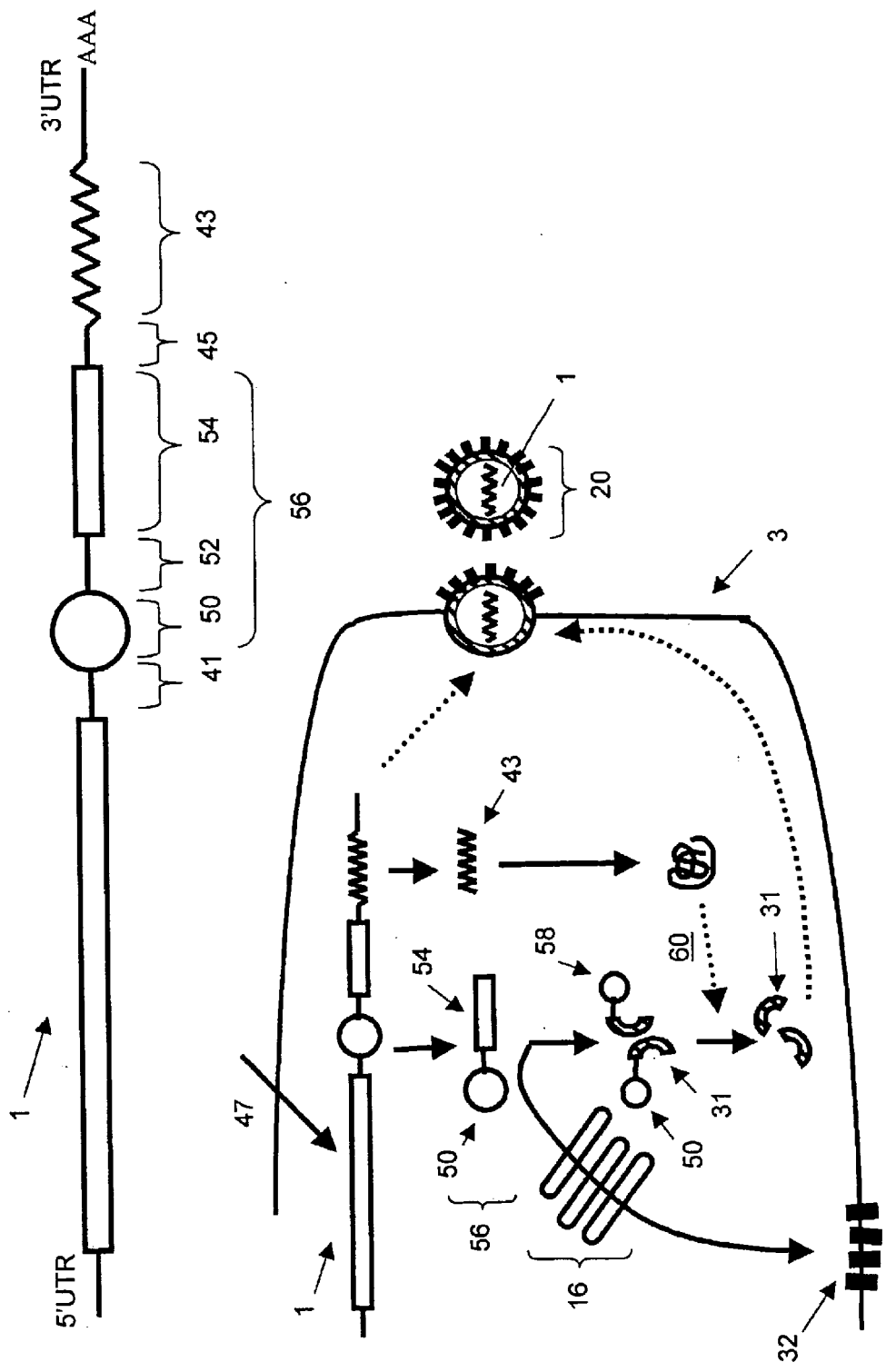
FIG. 3B schematizes a modified viral genome and a method for using the same in order to select an exogenous nucleic acid encoding a protease or a protein that triggers a proteolytic activity.

As shown in FIG. 3B, according to a preferred embodiment of the invention, the modified Sindbis virus genome (1) comprises a first subgenomic promoter (41) which corresponds to the naturally occurring sequence truncated 5 nucleotides after the site of initiation of transcription. The first subgenomic promoter (41) serves to express a messenger (56) encoding a fetter protein (50) fused to a structural proteins precursor (54). The fetter protein (50) and the structural proteins precursor (54) are separated by a protease cleavage site (52) such that processing of the precursor (54) gives rise to functional envelope proteins (32) and to a fusion protein (58) consisting of the fetter protein (50) fused to the N-terminus of the capsid protein (31). The production of such fusion protein (58) will impair the ability of the capsid protein (31) to encapsidate the recombinant viral genome (1). The second subgenomic promoter (45) corresponds to 46 nucleotides upstream and 14 nucleotides downstream of the site of initiation of transcription and serves to express an exogenous nucleic acid (43).

Upon transfection (47) in a suitable host (3), only recombinant Sindbis genome (1) comprising an exogenous nucleic acid (43) of interest will eventually result in the production of recombinant viral particles (20). Such exogenous nucleic acid (43) must encode or trigger the activation of a proteolytic activity capable of cleaving (60) the fetter protein (50) in order to liberate the capsid protein (31) from the fetter protein (50).

ii) Plasmid Construction

Figure 9A:
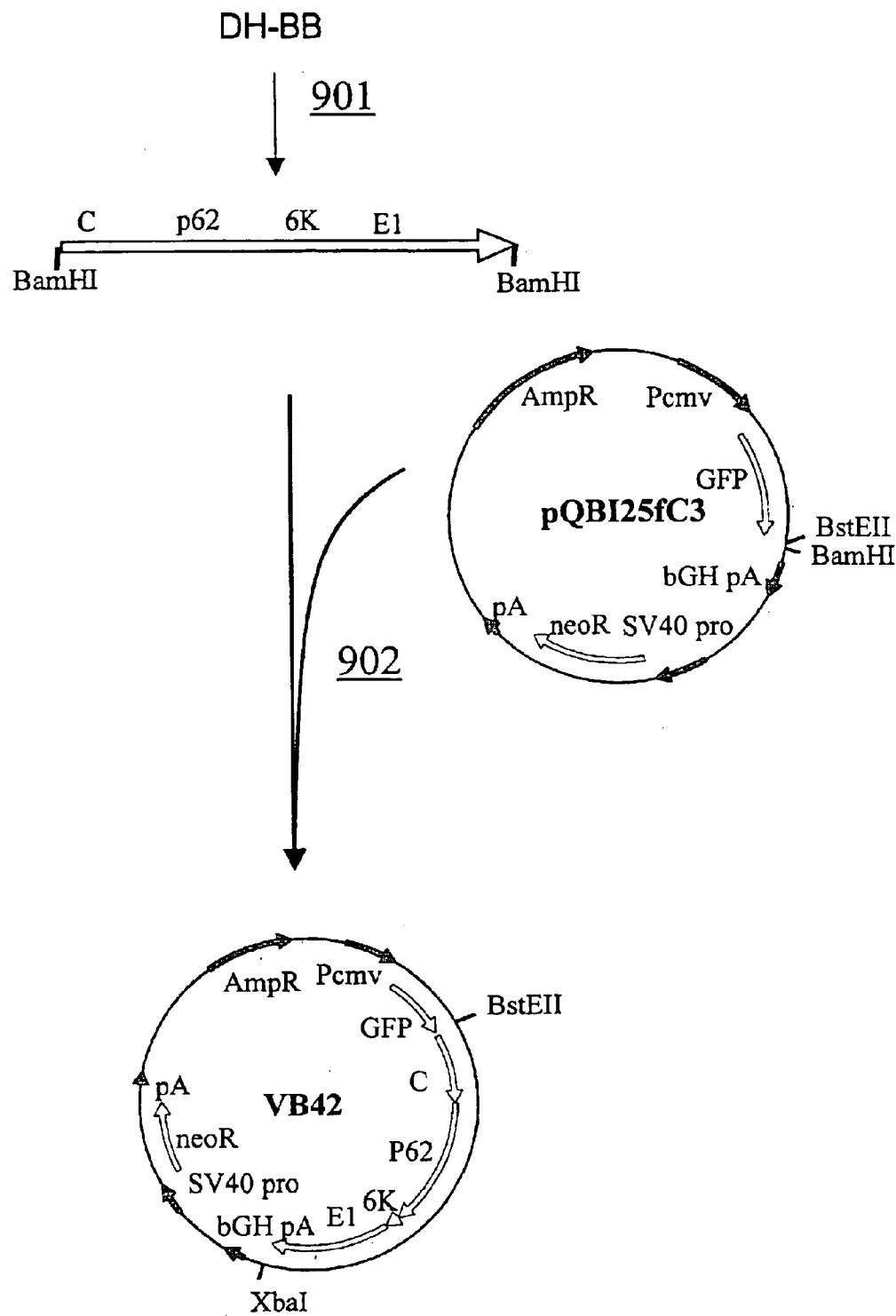
Figure 9B:
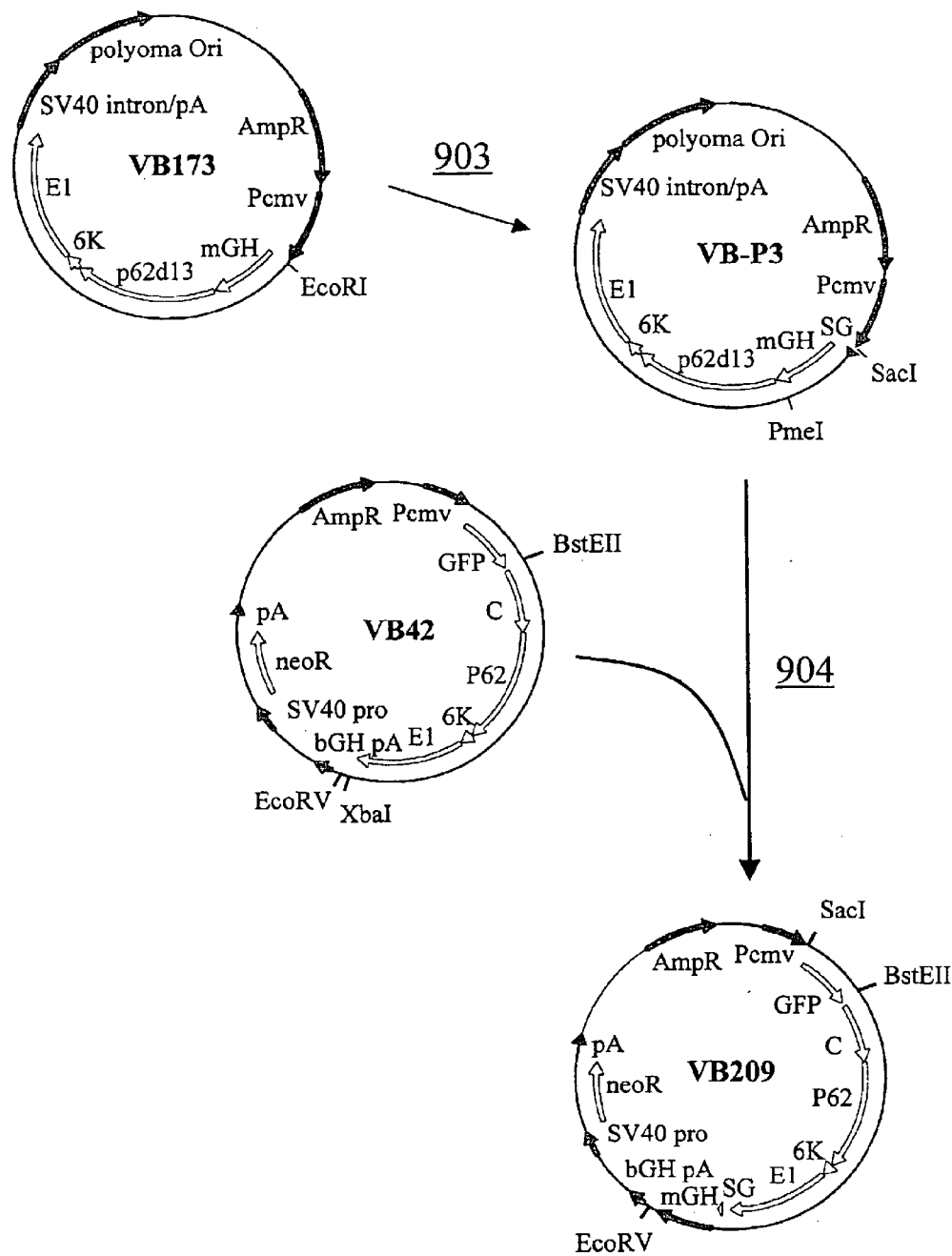
Figure 9C:
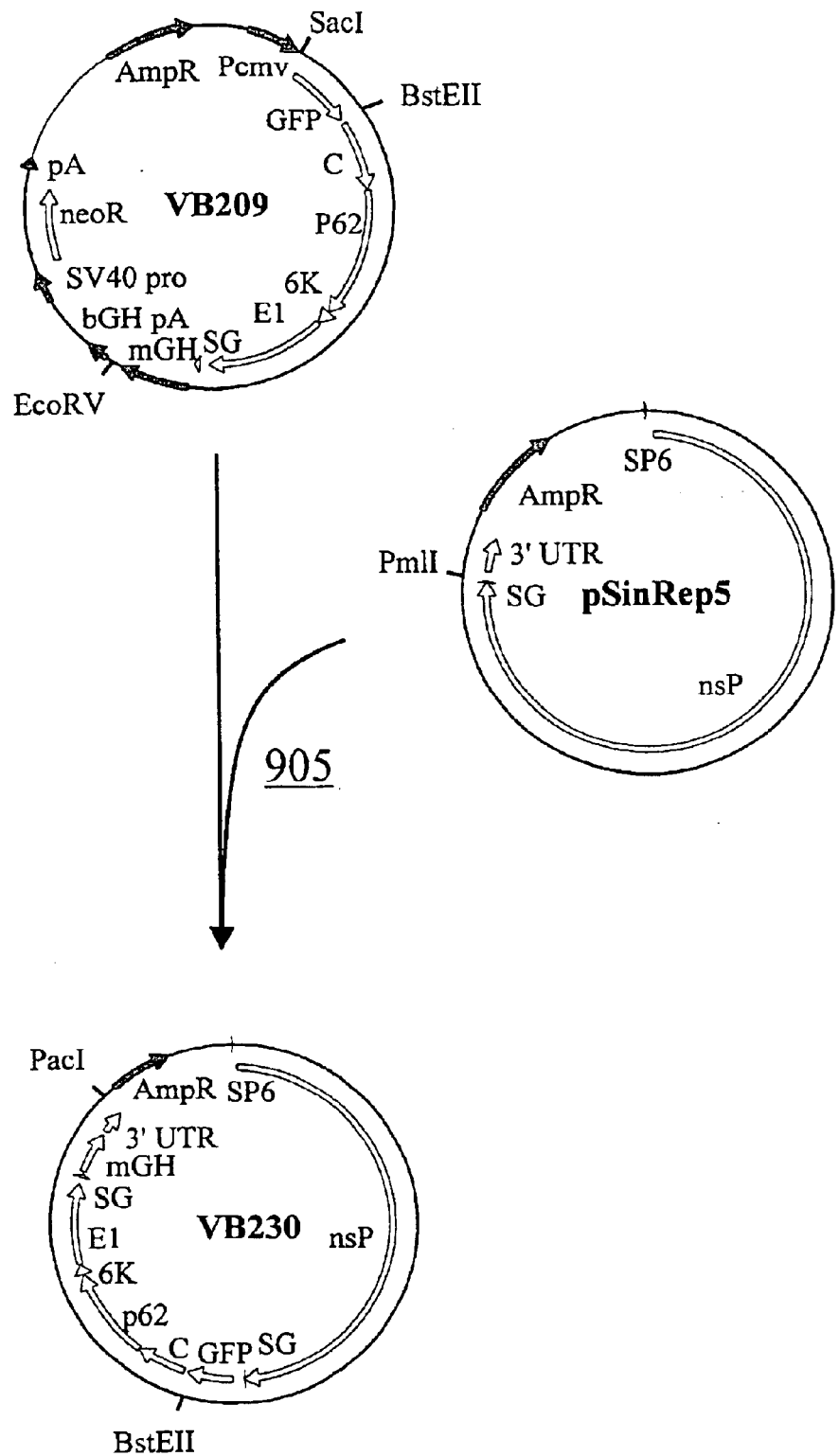

The process of plasmid construction is schematized on FIG. 9. The Sindbis structural proteins coding sequence was amplified by PCR starting from DH-BB, using forward primer 24-1V (see Materials and Methods) and reverse primer 25-1V (5'-tctagagatgcattatgcacatcag-3'; SEQ ID NO:17) (901). The PCR product was digested with BamHI and cloned into BamHI-digested pQBI25fC3 (Quantum Biotechnology, Montreal, Quebec, Canada), thereby inserting the structural proteins coding sequence downstream and in-frame with the one of green fluorescent protein ("GFP") (902). To prevent the translation of unfettered structural proteins (e.g. by spurious initiation), the first methionine of the capsid protein was removed in the cloning process. A double-stranded oligonucleotide (5'-tccaagccatcagaggggaaataaagcatctctacggtggtcctaaatagtcagcatagt-3' (strand A; SEQ ID NO:18) annealed to 5'-actatgctgactatttaggaccaccgtagagatgctttatttcccctctgatggcttgga-3'; SEQ ID NO:19) corresponding to nucleotides −46/+14 of the Sindbis subgenomic promoter (numbering relative to the transcription start site) was cloned in the blunted EcoRI site of VB173 to generate VB-P3 (903). A SacI-PmeI fragment of VB-P3 was blunted, isolated and cloned into the unique and blunted XbaI site of VB42 to generate VB209 (904). A SacI-EcoRV fragment of VB209 was isolated, blunted, and cloned into PmlI-digested pSinRep5 (905). The resulting construct (VB230) contains a unique BstEII site at the junction of GFP and the capsid protein to introduce a nucleic acid coding for the protease cleavage site. Insertion of said nucleic acid (e.g. double-stranded oligonucleotide) should maintain the reading frame between the fetter protein and the structural protein.

iii) Establishment of Suppressive Condition

The following experiment was performed in order to verify that fusion of GFP to the N-terminus of the capsid protein would impair production of viral particles. Cells were transfected with modified viral genomes transcribed either from VB230 or from a control plasmid (VB222, see Example 3 below). The modified viral genome transcribed from the control plasmid expresses the normal structural proteins from the first subgenomic promoter and GFP from the second subgenomic promoter, thereby allowing the production of infectious viral particles. Expression of GFP, whether fused to the capsid protein (VB230) or not (VB222), allows for simple detection of transfected and/or infected cells by means of fluorescence microscopy. Medium was changed 13 hours after transfection and left on the cells for 1 hour to accumulate viral particles. In this one hour period, cells transfected with viral genome transcribed from VB222 produced 38,000 plaque forming units/ml whereas cells transfected with modified viral genome transcribed from VB230 produced 433 plaque forming units/ml. This 87-fold decrease shows that fusion of a fetter protein to the capsid protein severely impairs production of viral particles.

D) Example 3

Method for Selecting Nucleic Acid Encoding a Drug-resistance Proteins or Peptides i) Background and Strategy In a third embodiment, the invention foresees the selection of nucleic acids encoding drug-resistance proteins or peptides. Indeed, a number of conditions has been reported to affect the viral functions and more particularly packaging functions of the structural proteins of Alphaviruses. These conditions include incubation of infected cells in low salt medium or treatment of infected cells with drugs that interfere with the normal post-translational processing of viral envelope proteins. Known post-translational processing of Sindbis envelope proteins include glycosylation (p62 and E1), acylation (p62 and E1), and phosphorylation/dephosphorylation (p62).

More specifically, it has been reported that treatment of Sindbis-infected BHK-21 cells with 30 μg/ml of cerulenin impairs production of viral particles. It has been suggested that cerulenin, a drug that inhibits fatty acid synthesis, acts by preventing the acylation of the cytosolic tail of p62. It has also been reported that treatment of Sindbis-infected BHK-21 cells with 200 nM of okadaic acid impairs production of viral particles. Okadaic acid is a drug that inhibits PP2A, a phosphatase involved in dephosphorylation of proteins, and it has been suggested that this drug impairs production of viral particles by preventing the dephosphorylation of the cytosolic tail of p62.

It is thus possible to test whether the above mentioned conditions can impair the production of viral particles and it is therefore conceivable to use the method of the invention to screen and select exogenous nucleic acids encoding drug-resistance proteins or peptides.

According to a most preferred embodiment, the method of the invention to identify exogenous nucleic acids encoding drug-resistance proteins or peptides would comprise the following steps:

a) a library of exogenous nucleic acids, preferably cDNAs, would be cloned into a unique restriction site (e.g. BamHI) immediately downstream of the second subgenomic promoter of a Sindbis genome modified as described below;

b) a suitable host would be transfected with the cloned library of step a);

c) the transfected host of step b) would be treated with a given drug of interest. The drug should be used at an effective concentration such that it effectively inhibits production of viral particles from a control recombinant viral genome. A suitable control recombinant viral genome could be a viral genome comprising an exogenous nucleic acid encoding a protein known not to have drug-resistance function such as GFP.

d) according to this method, the production of viral particles would therefore be indicative that an exogenous nucleic acid encoding a drug-resistance protein or peptide has been inserted in step a) and the viral particles so produced would be collected and preferably propagated in the presence of the drug;

e) finally, it would be highly preferable to identify the exogenous nucleic acids contained within the viral particles produced.

Figure 3C:
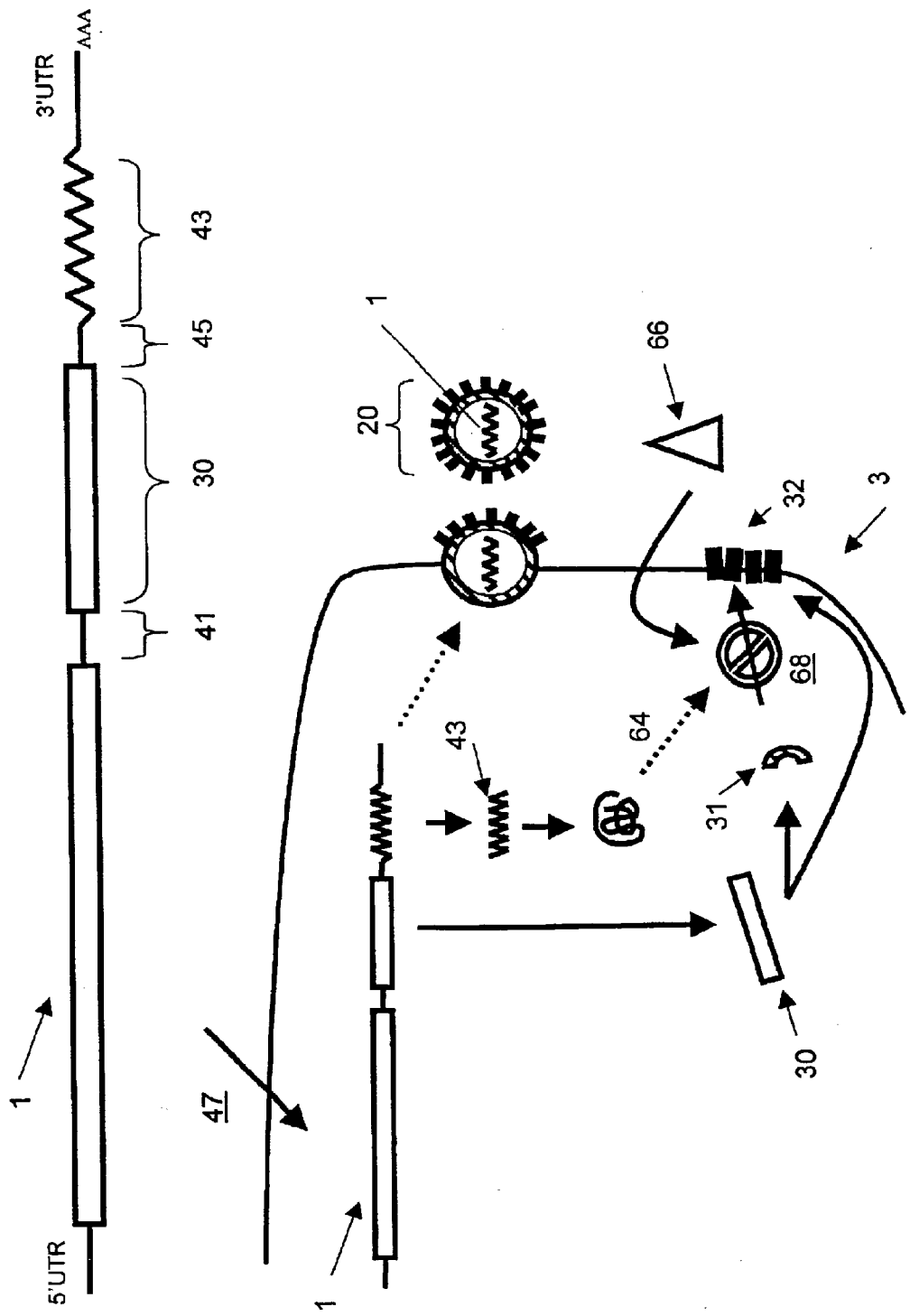
FIG. 3C schematizes a modified viral genome and a method for using the same in order to select an exogenous nucleic acid encoding a drug-resistance protein.
Figure 4A:
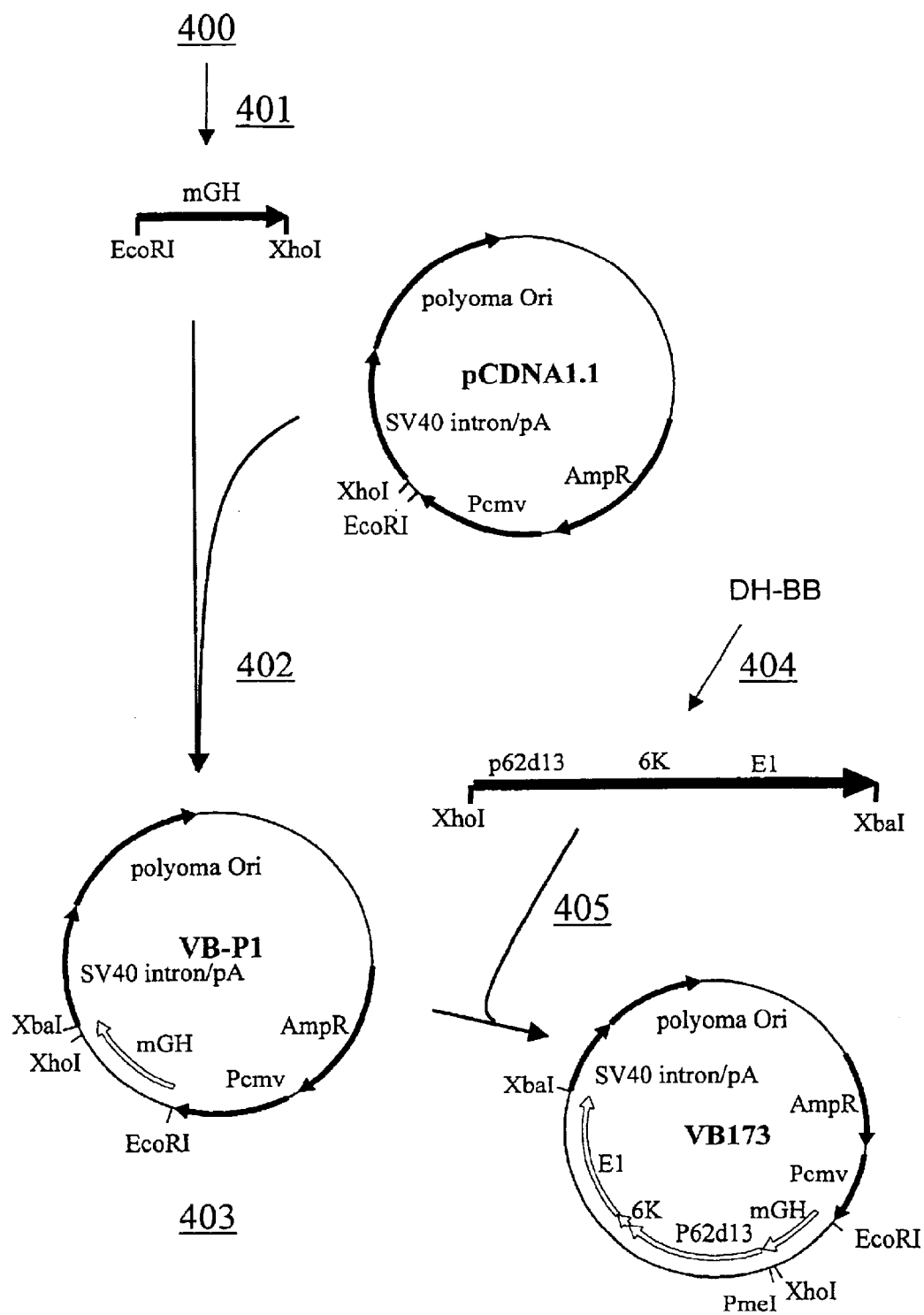
FIGS. 4A, 4B, 4C, and 4D schematize the cloning process of a plasmid containing a modified viral genome used to select an exogenous nucleic acid encoding a signal peptide.
Figure 4B:
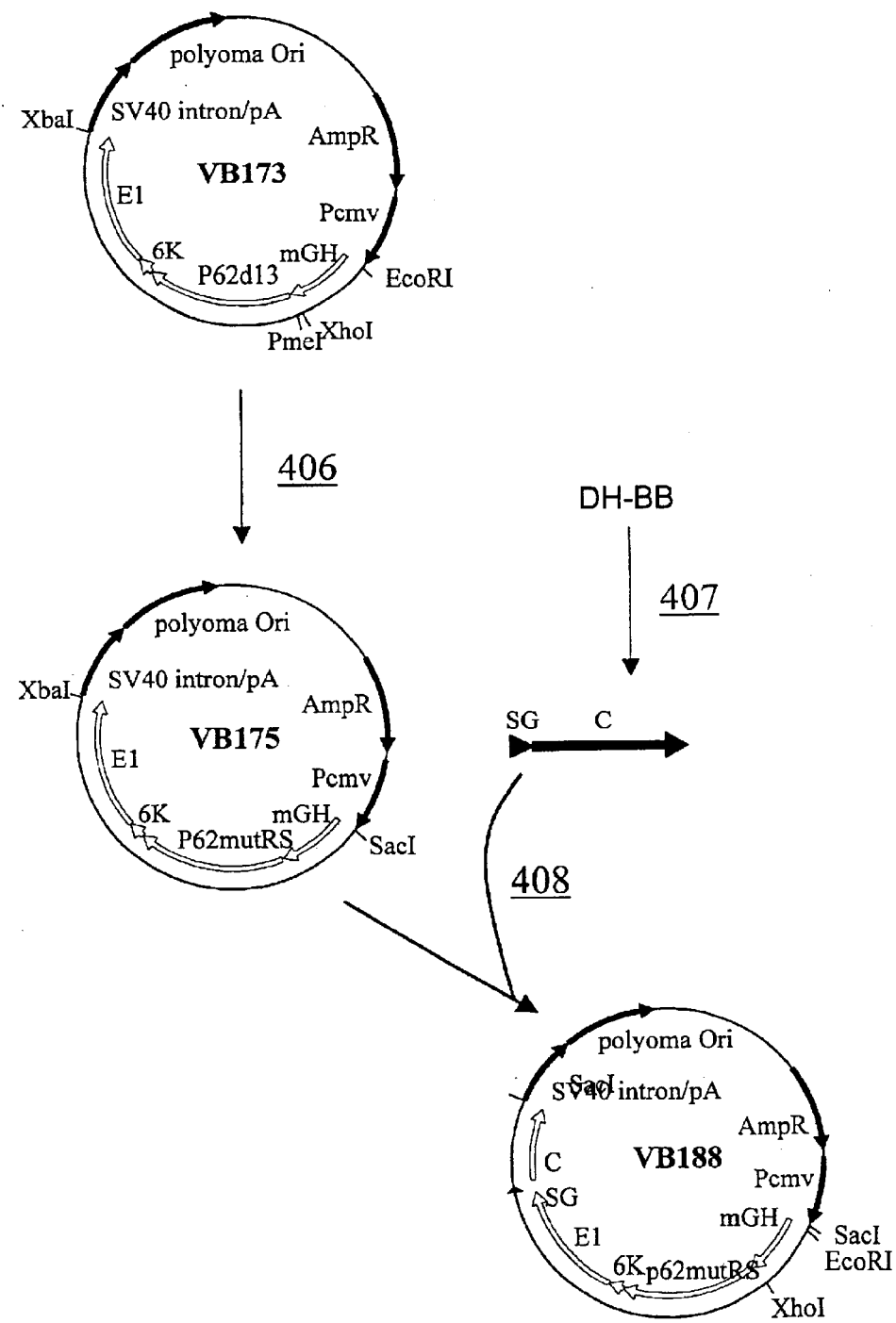
Figure 4C:
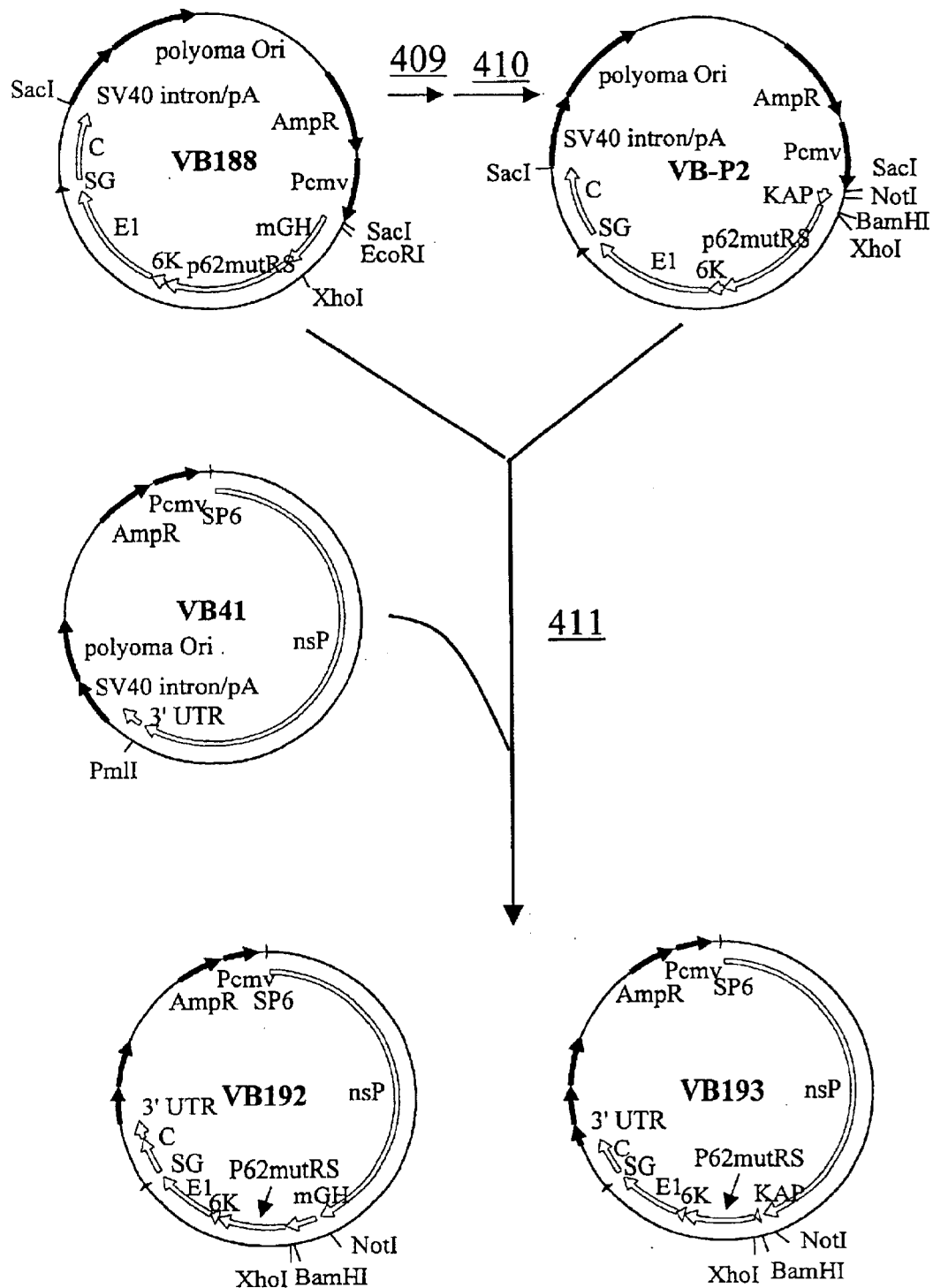
Figure 4D:
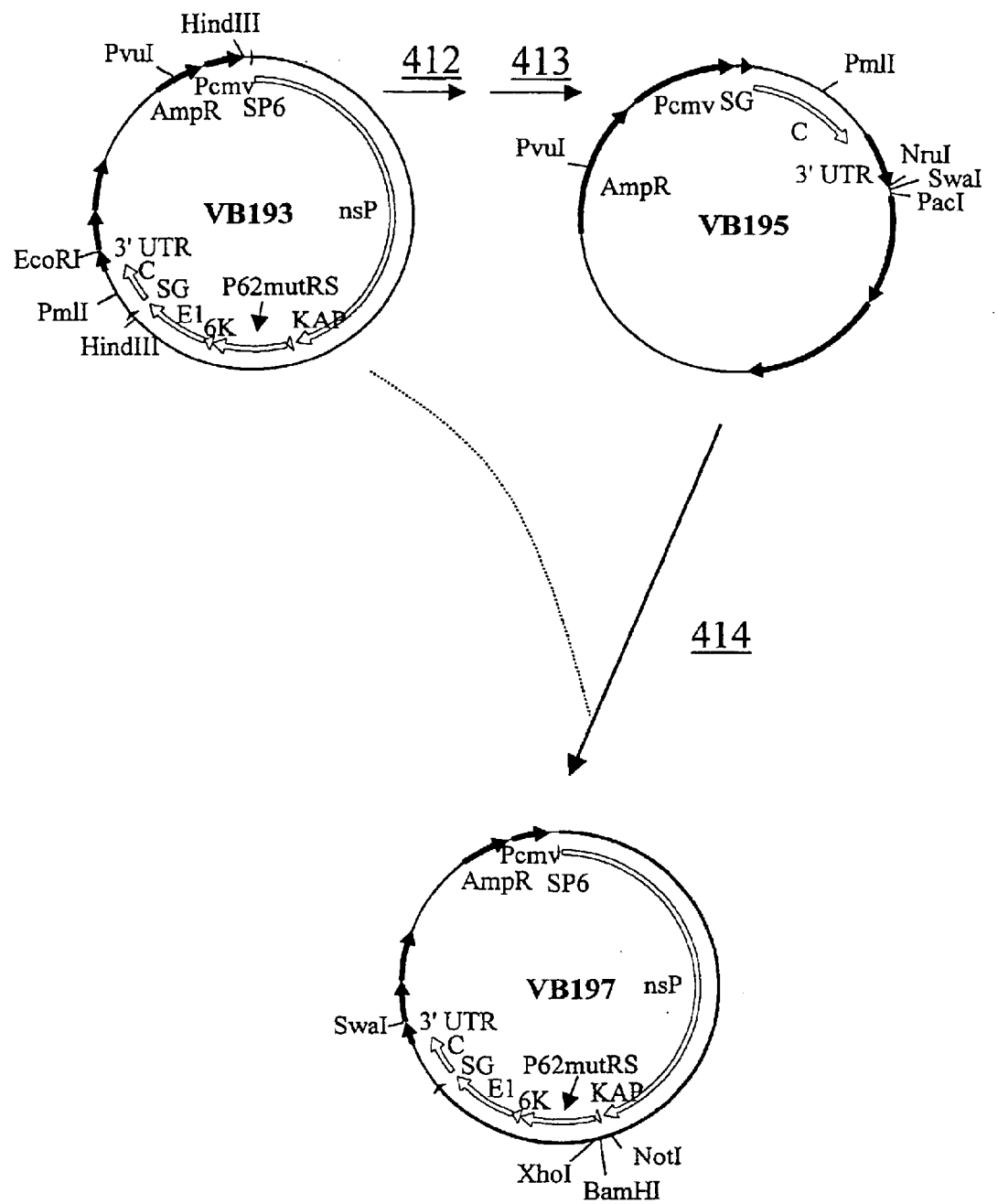
Figure 6:
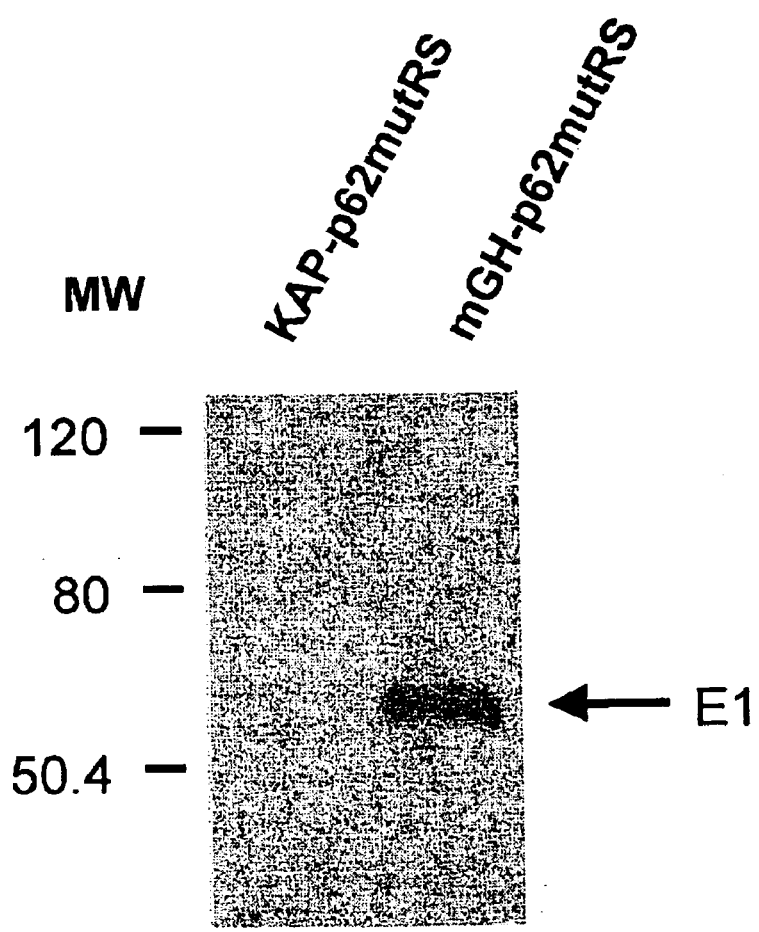
FIG. 6 is a picture of a Western blot showing the presence or the absence of the E1 protein at the cell membrane after transfection of a plasmid encoding a keratin-associated protein fragment fused to the mutated envelope proteins (KAP-p62mutRS) or a plasmid encoding a mouse growth hormone fragment fused to the mutated envelope proteins (mGH-p62mutRS). MW represents the migration of molecular weight markers in kilodaltons.
Figure 7:
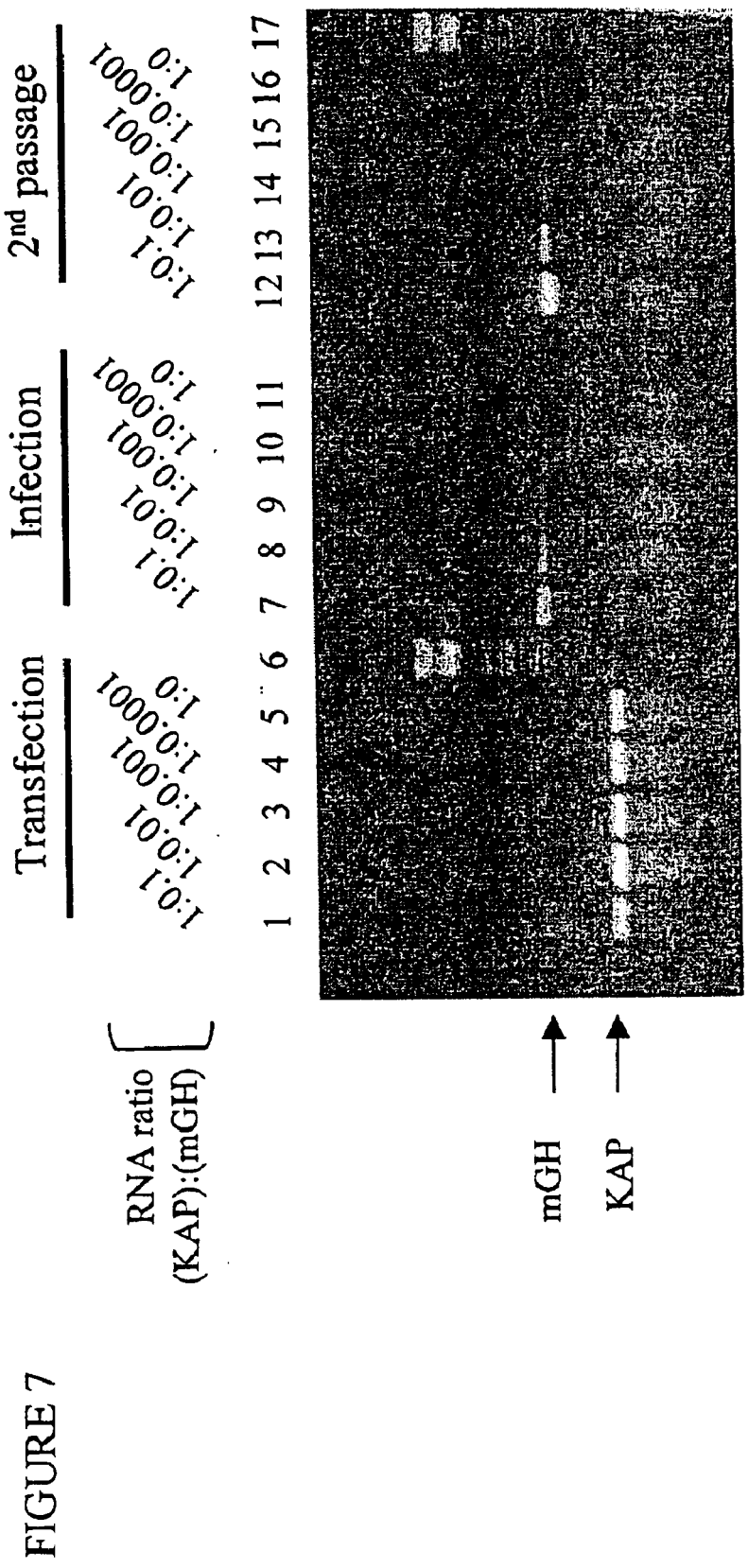
FIG. 7 is a picture of an agarose gel showing the results of RT-PCR experiments in order to detect exogenous nucleic acids inserted into modified viral genomes after transfection (lanes 1 to 5) at decreasing ratios of modified viral genomes containing an exogenous nucleic acid encoding (mGH) or not (KAP) a signal peptide fused to mutated p62. Also shown are the results of RT-PCR on cells infected with viral particles collected after transfection (lanes 7–11) or with viral particles collected after a first passage (lanes 12–16). In all cases, RT-PCR was performed with total RNA extracted from cells. Lanes 6 and 17 show the migration of a molecular weight marker (lambda DNA digested with HindIII and EcoRI).

According to an hypothetical example shown in FIG. 3C, the modified Sindbis genome (1) would preferably comprise a first subgenomic promoter (41) corresponding to the naturally occurring sequence truncated 5 nucleotides after the site of initiation of transcription. It would also preferably comprise a second subgenomic promoter (45) corresponding to 46 nucleotides upstream and 14 nucleotides downstream of the site of initiation of transcription. The first subgenomic promoter (41) would serve to express a sequence encoding viral structural proteins (30). The second subgenomic promoter (45) would serve to express an exogenous nucleic acid (43) inserted into the viral genome (1).

Upon transfection (47) in a suitable host (3), the recombinant viral genome would express the exogenous nucleic acid (43) and a viral structural proteins messenger (30) encoding the capsid protein (31) and the envelope proteins (32). Upon treatment of transfected cells with a drug (66) that can inhibit in some way (68) production and/or release of viral particles (20), only recombinant Sindbis genome (1) comprising an exogenous nucleic acid (43) encoding or triggering the activation of a cellular activity capable of inactivating the suppressive property of the drug (64) could result in the production of recombinant viral particles (20). Alternatively, the exogenous nucleic acid (43) could act as an antisense RNA to inhibit translation of an endogenous messenger whose product is involved in the suppressive property of the drug.

ii) Experimentation of the Method

Figure 10A:
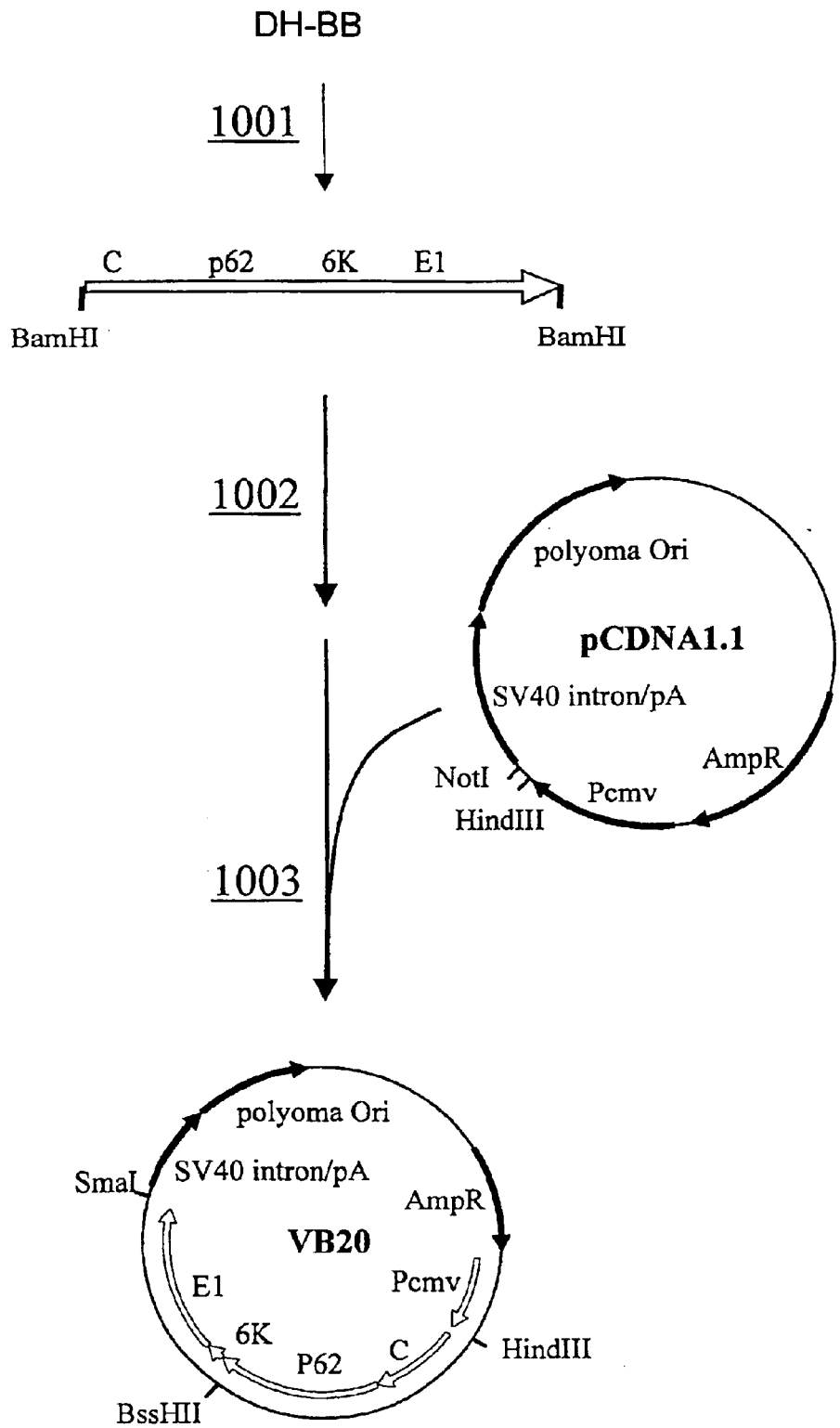
FIGS. 10A, 10B and 10C schematize the cloning process of a plasmid containing a modified viral genome used to select an exogenous nucleic acid encoding a drug-resistance protein.
Figure 10B:
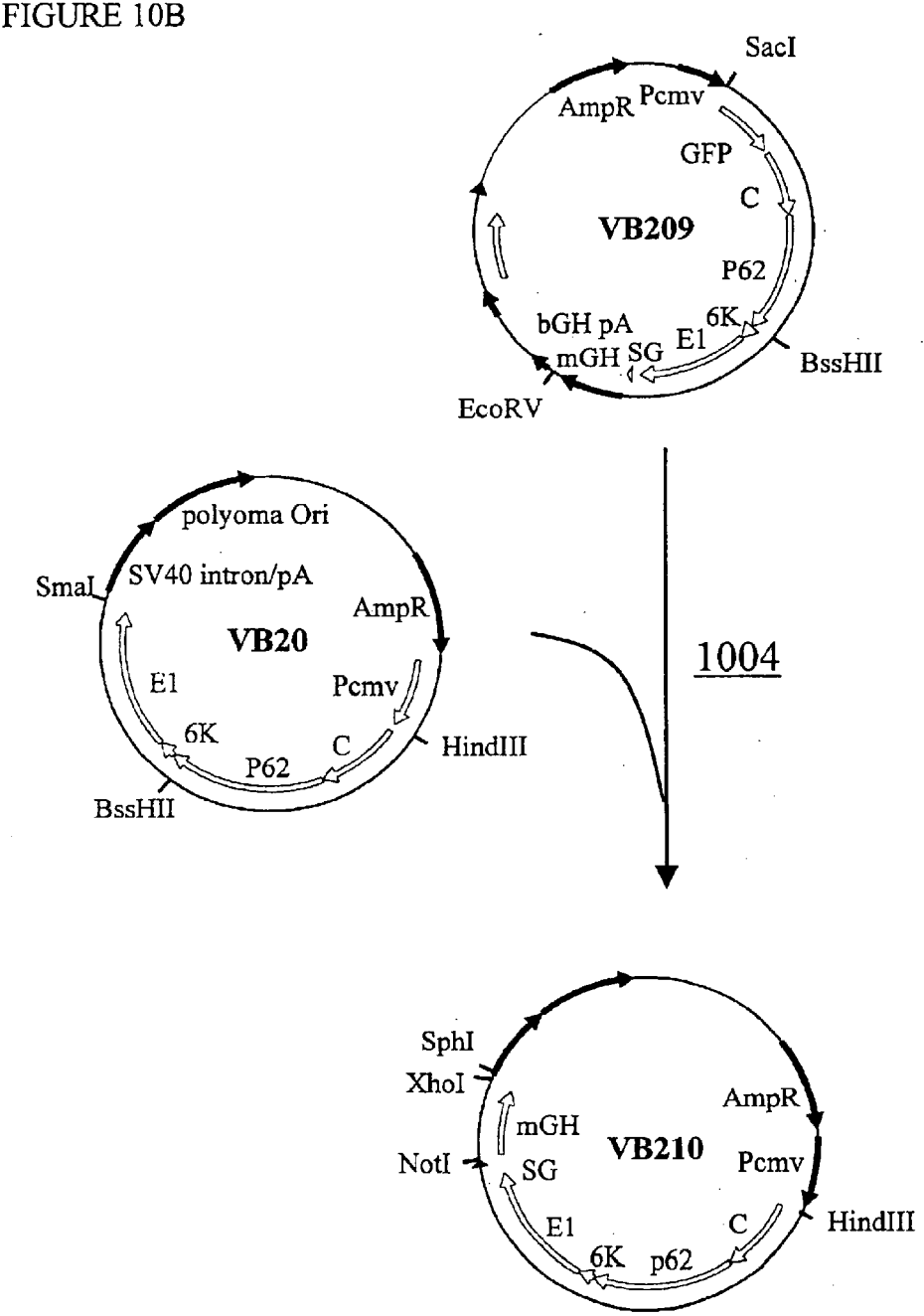
Figure 10C:
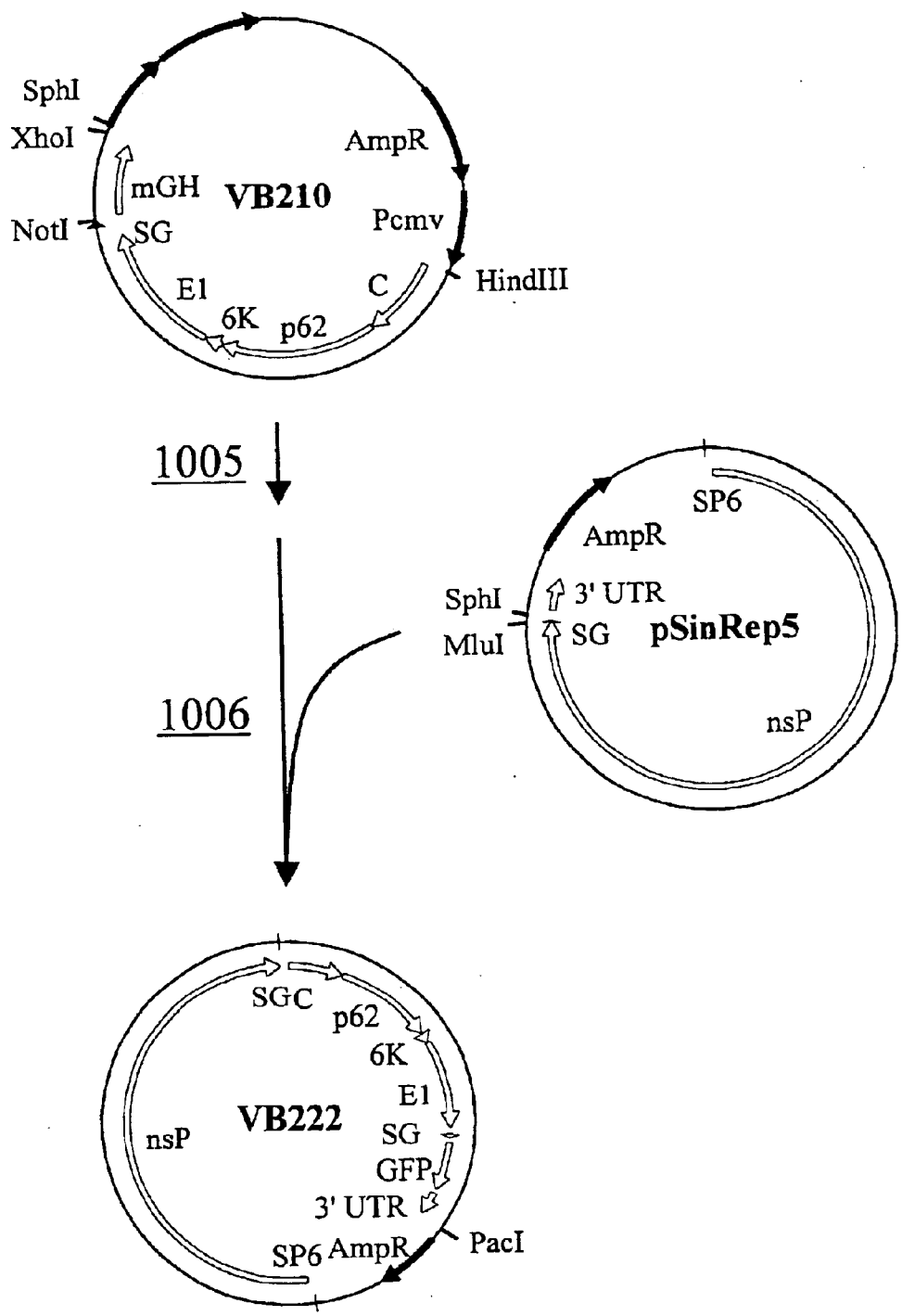

In order to ascertain that cerulenin and okadaic acid can impair production of viral particles from a modified Sindbis genome, we have constructed a modified Sindbis genome expressing a messenger encoding the structural proteins and a messenger encoding a marker protein, i.e. GFP. Construction of this plasmid is schematized on FIGS. 10A, 10B, and 10C. The Sindbis structural proteins coding sequence was amplified by PCR starting from DH-BB, using forward primer 20-1V (5'-tagtcagcatagtacatttc-3'; SEQ ID NO:20) and reverse primer 25-1V (1001). The PCR product was cloned into EcoRV-digested pBlueScript KS II (1002). A HindIII-NotI fragment of the resulting plasmid was cloned into HindIII-NotI-digested pcDNA1.1 (Invitrogen, Carlsbad, Calif.) to generate VB20 (1003). A BssHII-SmaI fragment of VB20 was cloned into BssHII-EcoRV-digested VB209 to generate VB210 (1004). A NotI-XhoI mGH fragment was replaced with a fragment containing the GFP coding sequence (1005). The resulting plasmid was digested with HindIII, blunted and further digested with SphI. A HindIII blunted-SphI fragment was cloned into pSinRep5 that had been previously digested with MluI, blunted and further digested with SphI (1006). The resulting construct (VB222) can be used to synthesize RNA copies of a Sindbis replicon encoding the structural proteins and a marker protein (i.e. GFP)

The viral genome was transcribed from plasmid VB222. The exogenous nucleic acid encodes GFP to facilitate detection of transfected and/or infected cells. BHK-21 cells were transfected with said viral genome and viral particles were collected 34 hours later. These viral particles were tittered by standard plaque assay and used to infect BHK-21 cells at a multiplicity of infection of 0.05. The medium was changed one hour post-infection. Drugs were added one hour post-infection at a concentration of 200 nM (okadaic acid) or 30 μg/ml (cerulenin) and viral particles were collected 6 hours later. Treatment of transfected cells with cerulenin resulted in a 39-fold decrease in virus production whereas treatment of transfected cells with okadaic acid resulted in a 13-fold decrease in virus production. Treatment with the drug could be maintained while propagating the viral particles, thereby further decreasing the number of viral particles produced from viral genomes expressing an exogenous nucleic acid encoding a peptide or protein that is not involved in drug-resistance.

These results indicate that treatment with certain drugs can impair production of viral particles and could be used to establish a suppressive condition for the present invention.

Throughout this paper, reference is made to a number of articles of scientific literature which are listed below and are incorporated herein by reference:

REFERENCES

Cho, Y.-G., Moon, H.-S., Sun, Y. C., (1997) Construction of hepatitis C-SIN virus recombinants with replicative dependency on hepatitis C virus serine protease activity, J. Virol. Meth., 65, 201–207.

Filocamo, G., Pacini, L., Migliaccio, G. (1997) Chimeric Sindbis viruses dependent on the NS3 protease of hepatitis C virus, J. Virol., 71, 1417–1427.

Strauss, E. G., Rice, C. M., Strauss, J. H. (1984) Complete nucleotide sequence of the genomic RNA of Sindbis virus, Virology, vol.133, 92–110

Tashiro, K., Tada, H., Heilker, R., Shirozu, M., Nakano, T., Honjo, T. (1993) Signal sequence trap: a cloning strategy for secreted proteins and type I membrane proteins, Science, 261, 600–602.

While several embodiments of the invention have been described, it will be understood that the present invention is capable of further modifications, and this application is intended to cover any variations, uses, or adaptations of the invention, following in general the principles of the invention and including such departures from the present disclosure as to come within knowledge or customary practice in the art to which the invention pertains, and as may be applied to the essential features hereinbefore set forth and falling within the scope of the invention or the limits of the appended claims.

TABLE 1

| # | Length (bp) | Number of inserts | Nucleotide sequence | Putative translation product | GenBank hit (accession no., description) | Presence of signal peptide |
|---|---|---|---|---|---|---|
| 1 | 132 | 25 | tgacccaggggctctgcaacacaaggagtctgc atgtctaagtggtagagatgctcagctttgtggata cgcggactctgttgctgcttgcagtaacttcgtgcct agcaacatgccaatatttgcaatcgg (SEQ ID NO 34) | MLSFVDTRTLLLLAVTSCLATCQ YLQSGSSSRSAAP . . . (SEQ ID NO. 38) | K01832 Mouse musculus procollagen, type 1, alpha 2 | Yes |
| 2 | 222 | 1 | ccacgctgtgcacaatgggttcctcgcaggcacc ccggatggggagtgtgggagggcacgggctgat ggcattgctgatggccggtcttattctgccaggaat cttggctaagagcattgggaccctctcggacccct gtaaggaccccacgaggatcacctccccgaatg acccttgtcattggaaagactggctccaacagc atcagcagccaaggtg (SEQ ID NO. 35) | MGSSQAPRMGSVGGHGLMALL MAGLILPGILAKSIGTLSDPCKDP TRITSPNDPCLIGKTGSNSISSQG GSSSRSAAP . . . (SEQ ID NO. 39) | NM_001264 Corneodesmosin | Yes |
| 3 | 132 | 2 | agcagcgttggcaccggcgaaccatggctggg attttctatttcatcctctttcgtttctctttggaatttgcg acgctgtcaccggttctagggtatacccgcgaat gaagttacttattggattcca (SEQ ID NO. 36) | MAGIFYFLFSFLFGICDAVTGSRV YPANEVTLLDSRSSSRSAAP . . . (SEQ ID NO. 40) | NM_007936 | Yes |
| 4 | 262 | 1 | gccatttatgagacattaaacctgaaaatggaaa acagactcctcagagtcttcttagtctgggctgccc tgaccatggatggagcatcagccaaacaggatg gcctctgggaaagcaagtccagcagtgatgtttc atcttgccctgaagcctcgctggagattgtgggctc tctggcccgactgcctgatcaacaggatacagct caggatgccagtgttgaggtaaacagaggttttaa ggaagaaggaagcccagata (SEQ ID NO. 37) | MENRLLRVFLVWAALTMDGASA KQDGLWESKSSSDVSSCPEASL EIVGSLARLPDQQDTAQDASVEV NRGFKEEGSPDRSSSRSAAP . . . (SEQ ID NO. 41) | D78270 Golgi autoantigen golgin, subfamily a3 | Yes |
| 5 | 309 | 1 | cgagctctgacgaatcagatggcctgtcaactt cccaggtgggattgcttggagttaacagcctgaa cgcagagccccgaaagcagagcattcagggca agcagagaacaccctgcagaggttttccaagaa tccctcggcatggcaagacaaggctgtttcgggt cataccaggtaatatccttgttcacttttgccatcgg cgtcaatctctgcttaggattcacagcaagtcgaat taagagggccgaatgggatgaaggacctccca cagtgtatctgactctccatggaccaacacatctg (SEQ ID NO. 42) | MARQGCFGSYQVISLFTFAIGVN LCLGFTASRIKRAEWDEGPPTVL SDSPWTNTSGSSSRSAAP . . . (SEQ ID NO. 44) | AF123542 Phosphodiestera sel/Nucleotide pyrophosphatase 2 | Yes |
| 9 | 115 | 1 | cagagaatgaagccctgtacacaacaacag attcaaacgaggtgttcccttagcaaggctgaag attcagtctctggtatttggaatttggatgcagtcctt gtttttggatg (SEQ ID NO. 43) | MKTCQHNRFKRGVPLARLKIQS LVFGIWMQSLFLDGSSSRSAAP . . . (SEQ ID NO. 45) | NM_001264 Corneodesmosin | No |

What is claimed is:

1. A method for selecting a nucleic acid encoding a signal peptide or at least partially a protein having a signal peptide comprising:

a) providing a viral genome capable, when present in a suitable host, of expressing an exogenous nucleic acid inserted therein and also capable of producing a viral particle;

b) modifying said viral genome so that it encodes a dysfunctional signal peptide and production of a viral particle is dependent on insertion into said viral genome of an exogenous nucleic acid encoding a functional signal peptide or at least partially a protein having a signal peptide;

c) inserting an exogenous nucleic acid into said viral genome to provide a recombinant viral genome;

d) transfecting said recombinant viral genome into a suitable host; and e) allowing said recombinant viral genome to express said exogenous nucleic acid and produce a recombinant viral particle, whereby production of at least one recombinant viral particle is indicative that the exogenous nucleic acid inserted in step c) encodes a functional signal peptide or at least partially a protein having a signal peptide.

2. The method of claim 1, wherein in step b) said viral genome is modified in order to inactivate a viral gene product involved in the production of said viral particle(s).

3. The method of claim 1, wherein said viral genome is transfected into said suitable host in a RNA form.

4. The method of claim 1, wherein said viral genome is in a cDNA form and is incorporated into a vector.

5. The method of claim 4, wherein said vector is a plasmid.

6. The method of claim 1, wherein said exogenous nucleic acid is taken from a library of nucleic acids.

7. The method of claim 6, wherein said library of nucleic acids comprises nucleic acids selected from cDNAs, cDNA fragments, genomic DNA fragments, antisense RNAs, and oligonucleotides.

8. The method of claim 1, wherein said viral genome encodes an Alphavirus.

9. The method of claim 8, wherein said Alphavirus is a Sindbis virus or a Semliki Forest virus.

10. The method of claim 1, wherein the viral genome of step a) is also capable of autoreplication and wherein insertion in step c) of an exogenous nucleic acid encoding a signal peptide or at least partially a protein having a signal peptide results in the production of a clonal population of recombinant viral particles.

11. The method of claim 10, wherein the recombinant viral particles produced are infectious.

12. The method of claim 1, further comprising a step selected from the group consisting of: (i) isolating said recombinant viral particle; (ii) propagating said recombinant viral particle; (iii) identifying the function of said exogenous nucleic acid; (iv) identifying the product expressed by said exogenous nucleic acid; and (v) sequencing at least partially the exogenous nucleic acid found into said recombinant viral particle.

* * * * *

SEQUENCE LISTING

<160> NUMBER OF SEQ ID NOS: 45

<210> SEQ ID NO 1
<211> LENGTH: 24
<212> TYPE: DNA
<213> ORGANISM: Artificial Sequence
<220> FEATURE:
<223> OTHER INFORMATION: sequence is completely synthesized

<400> SEQUENCE: 1
ggatccaata gaggattctt taac                                             24

<210> SEQ ID NO 2
<211> LENGTH: 21
<212> TYPE: DNA
<213> ORGANISM: Artificial Sequence
<220> FEATURE:
<223> OTHER INFORMATION: sequence is completely synthesized

<400> SEQUENCE: 2
tcaccactct tctgtccctt c                                                21

-continued

<210> SEQ ID NO 3
<211> LENGTH: 25
<212> TYPE: DNA
<213> ORGANISM: Artificial Sequence
<220> FEATURE:
<223> OTHER INFORMATION: sequence is completely synthesized

<400> SEQUENCE: 3
ggatcctacg aacatgcgac cactg                                    25

<210> SEQ ID NO 4
<211> LENGTH: 21
<212> TYPE: DNA
<213> ORGANISM: Artificial Sequence
<220> FEATURE:
<223> OTHER INFORMATION: sequence is completely synthesized

<400> SEQUENCE: 4
tcatcttcgt gtgctagtca g                                        21

<210> SEQ ID NO 5
<211> LENGTH: 30
<212> TYPE: DNA
<213> ORGANISM: Artificial Sequence
<220> FEATURE:
<223> OTHER INFORMATION: sequence is completely synthesized

<400> SEQUENCE: 5
agcgaattcg tcctgtggac agatcactgc                               30

<210> SEQ ID NO 6
<211> LENGTH: 30
<212> TYPE: DNA
<213> ORGANISM: Artificial Sequence
<220> FEATURE:
<223> OTHER INFORMATION: sequence is completely synthesized

<400> SEQUENCE: 6
gctctcgagg aaggcacagc tgctttccac                               30

<210> SEQ ID NO 7
<211> LENGTH: 30
<212> TYPE: DNA
<213> ORGANISM: Artificial Sequence
<220> FEATURE:
<223> OTHER INFORMATION: sequence is completely synthesized

<400> SEQUENCE: 7
cttctcgagc agtttaaacg tgagcttccc                               30

<210> SEQ ID NO 8
<211> LENGTH: 30
<212> TYPE: DNA
<213> ORGANISM: Artificial Sequence
<220> FEATURE:
<223> OTHER INFORMATION: sequence is completely synthesized

<400> SEQUENCE: 8
acgtctagat catcttcgtg tgctagtcag                               30

<210> SEQ ID NO 9
<211> LENGTH: 47
<212> TYPE: DNA
<213> ORGANISM: Artificial Sequence
<220> FEATURE:

-continued

<223> OTHER INFORMATION: sequence is completely synthesized

<400> SEQUENCE: 9
tcgagcagat ctgcagcacc actggtcacg gcaatgtgtc ggagcgg          47

<210> SEQ ID NO 10
<211> LENGTH: 43
<212> TYPE: DNA
<213> ORGANISM: Artificial Sequence
<220> FEATURE:
<223> OTHER INFORMATION: sequence is completely sunthesized

<400> SEQUENCE: 10
ccgctccgac acattgccgt gaccagtggt gctgcagatc tgc              43

<210> SEQ ID NO 11
<211> LENGTH: 60
<212> TYPE: DNA
<213> ORGANISM: Artificial Sequence
<220> FEATURE:
<223> OTHER INFORMATION: sequence is completely synthesized

<400> SEQUENCE: 11
gtgtccaagc catcagaggg gaaataaagc atctctacgg tggtcctaaa tagtcagcat    60

<210> SEQ ID NO 12
<211> LENGTH: 28
<212> TYPE: DNA
<213> ORGANISM: Artificial Sequence
<220> FEATURE:
<223> OTHER INFORMATION: sequence is completely synthesized

<400> SEQUENCE: 12
ccagagctca tgcggaccac tcttctgt                               28

<210> SEQ ID NO 13
<211> LENGTH: 24
<212> TYPE: DNA
<213> ORGANISM: Artificial Sequence
<220> FEATURE:
<223> OTHER INFORMATION: sequence is completely synthesized

<400> SEQUENCE: 13
tcgcgattta aattaattaa gctt                                   24

<210> SEQ ID NO 14
<211> LENGTH: 24
<212> TYPE: DNA
<213> ORGANISM: Artificial Sequence
<220> FEATURE:
<223> OTHER INFORMATION: sequence is completely synthesized

<400> SEQUENCE: 14
aagcttaatt aatttaaatc gcga                                   24

<210> SEQ ID NO 15
<211> LENGTH: 18
<212> TYPE: DNA
<213> ORGANISM: Artificial Sequence
<220> FEATURE:
<223> OTHER INFORMATION: sequence is completely synthesized

<400> SEQUENCE: 15
agacgcgtag atctcacc                                          18

```
<210> SEQ ID NO 16
<211> LENGTH: 20
<212> TYPE: DNA
<213> ORGANISM: Artificial Sequence
<220> FEATURE:
<223> OTHER INFORMATION: sequence is completely synthesized

<400> SEQUENCE: 16
gatccgcacc gcaatatggc                                          20

<210> SEQ ID NO 17
<211> LENGTH: 25
<212> TYPE: DNA
<213> ORGANISM: Artificial Sequence
<220> FEATURE:
<223> OTHER INFORMATION: sequence is completely synthesized

<400> SEQUENCE: 17
tctagagatg cattatgcac atcag                                    25

<210> SEQ ID NO 18
<211> LENGTH: 60
<212> TYPE: DNA
<213> ORGANISM: Artificial Sequence
<220> FEATURE:
<223> OTHER INFORMATION: sequence is completely synthesized

<400> SEQUENCE: 18
tccaagccat cagaggggaa ataaagcatc tctacggtgg tcctaaatag tcagcatagt    60

<210> SEQ ID NO 19
<211> LENGTH: 60
<212> TYPE: DNA
<213> ORGANISM: Artificial Sequence
<220> FEATURE:
<223> OTHER INFORMATION: sequence is completely synthesized

<400> SEQUENCE: 19
actatgctga ctatttagga ccaccgtaga gatgctttat ttcccctctg atggcttgga    60

<210> SEQ ID NO 20
<211> LENGTH: 20
<212> TYPE: DNA
<213> ORGANISM: Artificial Sequence
<220> FEATURE:
<223> OTHER INFORMATION: sequence is completely synthesized

<400> SEQUENCE: 20
tagtcagcat agtacatttc                                          20

<210> SEQ ID NO 21
<211> LENGTH: 51
<212> TYPE: DNA
<213> ORGANISM: Artificial Sequence
<220> FEATURE:
<223> OTHER INFORMATION: sequence is completely synthesized

<400> SEQUENCE: 21
tcgatccgaa ttcgcggccg ctctattgga tcctcgagca gatctgcagc a            51

<210> SEQ ID NO 22
<211> LENGTH: 148
<212> TYPE: DNA
<213> ORGANISM: Artificial Sequence
<220> FEATURE:
<223> OTHER INFORMATION: sequence is completely synthesized
```

-continued

```
<400> SEQUENCE: 22
agatgaatca agcttatcga taccgtcgag catgcatcta ggtgtccaag ccatcagagg      60
ggaaataaag catctctacg gtggtcctaa atagtcagca tagtacattt catctgacta    120
atactacaac accaccacca tgaataga                                        148

<210> SEQ ID NO 23
<211> LENGTH: 18
<212> TYPE: DNA
<213> ORGANISM: Artificial Sequence
<220> FEATURE:
<223> OTHER INFORMATION: sequence is completely synthesized

<400> SEQUENCE: 23
gagtggtccg catggtga                                                    18

<210> SEQ ID NO 24
<211> LENGTH: 54
<212> TYPE: DNA
<213> ORGANISM: Artificial Sequence
<220> FEATURE:
<223> OTHER INFORMATION: sequence is completely synthesized

<400> SEQUENCE: 24
aaaaaaaaaa aaaaaaaaaa aaaaaaaaaa aagggggaatt tcgcgattta aatt           54

<210> SEQ ID NO 25
<211> LENGTH: 48
<212> TYPE: DNA
<213> ORGANISM: Sindbis virus
<220> FEATURE:
<223> OTHER INFORMATION: sequence is completely synthesized

<400> SEQUENCE: 25
tctgcagcac cactggtcac ggcaatgtgt ttgctcggaa atgtgagc                   48

<210> SEQ ID NO 26
<211> LENGTH: 16
<212> TYPE: PRT
<213> ORGANISM: Sindbis virus
<220> FEATURE:
<223> OTHER INFORMATION: sequence is completely synthesized

<400> SEQUENCE: 26

Ser Ala Ala Pro Leu Val Thr Ala Met Cys Leu Leu Gly Asn Val Ser
  1               5                  10                  15

<210> SEQ ID NO 27
<211> LENGTH: 48
<212> TYPE: DNA
<213> ORGANISM: Artificial Sequence
<220> FEATURE:
<223> OTHER INFORMATION: sequence is completely synthesized

<400> SEQUENCE: 27
tctgcagcac cactggtcac ggcaatgtgt cggagcggaa atgtgagc                   48

<210> SEQ ID NO 28
<211> LENGTH: 16
<212> TYPE: PRT
<213> ORGANISM: Artificial Sequence
<220> FEATURE:
<223> OTHER INFORMATION: sequence is completely synthesized

<400> SEQUENCE: 28
```

```
Ser Ala Ala Pro Leu Val Thr Ala Met Cys Arg Ser Gly Asn Val Ser
 1               5                   10                  15
```

<210> SEQ ID NO 29
<211> LENGTH: 44
<212> TYPE: DNA
<213> ORGANISM: Artificial Sequence
<220> FEATURE:
<223> OTHER INFORMATION: sequence is completely synthesized

<400> SEQUENCE: 29
gagagagaga gagtttaaac gtcgactttt ttttttttt tttt         44

<210> SEQ ID NO 30
<211> LENGTH: 34
<212> TYPE: DNA
<213> ORGANISM: Artificial Sequence
<220> FEATURE:
<223> OTHER INFORMATION: sequence is completely synthesized

<400> SEQUENCE: 30
gctaagcttg ctatcggcgg ccgcgagaat tcgt         34

<210> SEQ ID NO 31
<211> LENGTH: 30
<212> TYPE: DNA
<213> ORGANISM: Artificial Sequence
<220> FEATURE:
<223> OTHER INFORMATION: sequence is completely synthesized

<400> SEQUENCE: 31
acgaattctc gcggccgccg atagcaagct         30

<210> SEQ ID NO 32
<211> LENGTH: 16
<212> TYPE: PRT
<213> ORGANISM: Artificial Sequence
<220> FEATURE:
<223> OTHER INFORMATION: sequence is completely synthesized

<400> SEQUENCE: 32

```
Ser Ala Ala Pro Leu Val Thr Ala Met Cys Gly Ser Gly Asn Val Ser
 1               5                   10                  15
```

<210> SEQ ID NO 33
<211> LENGTH: 13
<212> TYPE: DNA
<213> ORGANISM: Artificial Sequence
<220> FEATURE:
<223> OTHER INFORMATION: sequence is completely synthesized

<400> SEQUENCE: 33
gagctcatgc gga         13

<210> SEQ ID NO 34
<211> LENGTH: 132
<212> TYPE: DNA
<213> ORGANISM: Mouse

<400> SEQUENCE: 34
tgacccaggg gctctgcaac acaaggagtc tgcatgtcta agtggtagag atgctcagct         60
ttgtggatac gcggactctg ttgctgcttg cagtaacttc gtgcctagca acatgccaat        120
atttgcaatc gg         132

<210> SEQ ID NO 35
<211> LENGTH: 222
<212> TYPE: DNA
<213> ORGANISM: Homo sapiens

<400> SEQUENCE: 35

```
ccacgctgtg cacaatgggt tcctcgcagg caccccggat ggggagtgtg ggagggcacg      60
ggctgatggc attgctgatg gccggtctta ttctgccagg aatcttggct aagagcattg     120
ggaccctctc ggaccctgt aaggacccca cgaggatcac ctccccgaat gaccccttgtc    180
tcattggaaa gactggctcc aacagcatca gcagccaagg tg                        222
```

<210> SEQ ID NO 36
<211> LENGTH: 132
<212> TYPE: DNA
<213> ORGANISM: Mouse

<400> SEQUENCE: 36

```
agcagcgttg gcaccggcga accatggctg ggattttcta tttcatcctc ttttcgtttc      60
tctttggaat ttgcgacgct gtcaccggtt ctagggtata ccccgcgaat gaagttactt     120
tattggattc ca                                                         132
```

<210> SEQ ID NO 37
<211> LENGTH: 262
<212> TYPE: DNA
<213> ORGANISM: Mouse

<400> SEQUENCE: 37

```
gccatttatg agacattaaa cctgaaaatg gaaaacagac tcctcagagt cttcttagtc      60
tgggctgccc tgaccatgga tggagcatca gccaaacagg atggcctctg ggaaagcaag     120
tccagcagtg atgtttcatc ttgccctgaa gcctcgctgg agattgtggg ctctctggcc     180
cgactgcctg atcaacagga tacagctcag gatgccagtg ttgaggtaaa cagaggtttt     240
aaggaagaag gaagcccaga ta                                              262
```

<210> SEQ ID NO 38
<211> LENGTH: 36
<212> TYPE: PRT
<213> ORGANISM: Mouse

<400> SEQUENCE: 38

```
Met Leu Ser Phe Val Asp Thr Arg Thr Leu Leu Leu Ala Val Thr
  1               5                  10                  15
Ser Cys Leu Ala Thr Cys Gln Tyr Leu Gln Ser Gly Ser Ser Ser Arg
                 20                  25                  30
Ser Ala Ala Pro
         35
```

<210> SEQ ID NO 39
<211> LENGTH: 78
<212> TYPE: PRT
<213> ORGANISM: Homo sapiens

<400> SEQUENCE: 39

```
Met Gly Ser Ser Gln Ala Pro Arg Met Gly Ser Val Gly Gly His Gly
  1               5                  10                  15
Leu Met Ala Leu Leu Met Ala Gly Ile Leu Pro Gly Ile Leu Ala Lys
                 20                  25                  30
Ser Ile Gly Thr Leu Ser Asp Pro Cys Lys Asp Pro Thr Arg Ile Thr
```

-continued

```
                35                  40                  45
Ser Pro Asn Asp Pro Cys Leu Ile Gly Lys Thr Gly Ser Asn Ser Ile
        50                  55                  60

Ser Ser Gln Gly Gly Ser Ser Arg Ser Ala Ala Ser Pro
65                  70                  75
```

<210> SEQ ID NO 40
<211> LENGTH: 44
<212> TYPE: PRT
<213> ORGANISM: Mouse

<400> SEQUENCE: 40

```
Met Ala Gly Ile Phe Tyr Phe Leu Phe Ser Phe Leu Phe Gly Ile Cys
1               5                   10                  15

Asp Ala Val Thr Gly Ser Arg Val Tyr Pro Ala Asn Glu Val Thr Leu
                20                  25                  30

Leu Asp Ser Arg Ser Ser Ser Arg Ser Ala Ala Pro
            35                  40
```

<210> SEQ ID NO 41
<211> LENGTH: 88
<212> TYPE: PRT
<213> ORGANISM: Mouse

<400> SEQUENCE: 41

```
Met Glu Asn Arg Leu Leu Arg Val Phe Leu Val Trp Ala Ala Leu Thr
1               5                   10                  15

Met Asp Gly Ala Ser Ala Lys Gln Asp Gly Leu Trp Glu Ser Lys Ser
                20                  25                  30

Ser Ser Asp Val Ser Ser Cys Pro Glu Ala Leu Ser Leu Glu Ile Val
            35                  40                  45

Gly Ser Leu Ala Arg Leu Pro Asp Gln Gln Asp Thr Ala Gln Asp Ala
        50                  55                  60

Ser Val Glu Val Asn Arg Gly Phe Lys Glu Glu Gly Ser Pro Asp Arg
65                  70                  75                  80

Ser Ser Ser Arg Ser Ala Ala Pro
                85
```

<210> SEQ ID NO 42
<211> LENGTH: 309
<212> TYPE: DNA
<213> ORGANISM: Mouse

<400> SEQUENCE: 42

```
cgagctctgc acgaatcaga tgcgcctgtc aacttcccag gtgggattgc ttggagttaa      60
cagcctgaac gcagagcccc gaaagcagag cattcagggc aagcagagaa caccctgcag     120
aggttttcca agaatccctc ggcatggcaa gacaaggctg tttcgggtca taccaggtaa     180
tatccttgtt cacttttgcc atcggcgtca atctctgctt aggattcaca gcaagtcgaa     240
ttaagagggc cgaatgggat gaaggacctc ccacagtgtt atctgactct ccatggacca     300
acacatctg                                                             309
```

<210> SEQ ID NO 43
<211> LENGTH: 114
<212> TYPE: DNA
<213> ORGANISM: Mouse

<400> SEQUENCE: 43

-continued

```
cagagaatga agccctgtac acaacacaac agattcaaac gaggtgttcc cttagcaagg     60
ctgaagattc agtctcggta tttggaattt ggatgcagtc cttgtttttg gatg          114

<210> SEQ ID NO 44
<211> LENGTH: 64
<212> TYPE: PRT
<213> ORGANISM: Mouse

<400> SEQUENCE: 44

Met Ala Arg Gln Gly Cys Phe Gly Ser Tyr Gln Val Ile Ser Leu Phe
  1               5                  10                  15

Thr Phe Ala Ile Gly Val Asn Leu Cys Leu Gly Phe Thr Ala Ser Arg
             20                  25                  30

Ile Lys Arg Ala Glu Trp Asp Glu Gly Pro Pro Thr Val Leu Ser Asp
         35                  40                  45

Ser Pro Trp Thr Asn Thr Ser Gly Ser Ser Ser Arg Ser Ala Ala Pro
     50                  55                  60

<210> SEQ ID NO 45
<211> LENGTH: 45
<212> TYPE: PRT
<213> ORGANISM: Mouse

<400> SEQUENCE: 45

Met Lys Thr Cys Thr Gln His Asn Arg Phe Lys Arg Gly Val Pro Leu
  1               5                  10                  15

Ala Arg Leu Lys Ile Gln Ser Leu Val Phe Gly Ile Trp Met Gln Ser
             20                  25                  30

Leu Phe Leu Asp Gly Ser Ser Ser Arg Ser Ala Ala Pro
         35                  40                  45
```